US007998720B2

(12) United States Patent
Jonniaux et al.

(10) Patent No.: US 7,998,720 B2
(45) Date of Patent: Aug. 16, 2011

(54) ENZYME WITH XYLANASE ACTIVITY

(75) Inventors: Jean-Luc Jonniaux, Tienen (BE);
Thierry Dauvrin, Couthuin (BE)

(73) Assignee: Puratos N.V., Groot-Bijgaarden (BE)

( * ) Notice: Subject to any disclaimer, the term of this patent is extended or adjusted under 35 U.S.C. 154(b) by 1412 days.

(21) Appl. No.: 11/418,376

(22) Filed: May 3, 2006

(65) Prior Publication Data

US 2008/0274231 A1 Nov. 6, 2008

Related U.S. Application Data

(63) Continuation-in-part of application No. 11/153,260, filed on Jun. 15, 2005, now abandoned, which is a continuation of application No. 09/790,070, filed on Feb. 21, 2001, now abandoned.

(30) Foreign Application Priority Data

Feb. 21, 2000 (EP) .................................. 00870028

(51) Int. Cl.
*C12N 9/24* (2006.01)
*C12N 1/00* (2006.01)
*C12C 11/00* (2006.01)
(52) U.S. Cl. ..................... 435/200; 435/243; 435/254.5; 426/11
(58) Field of Classification Search .................. None
See application file for complete search history.

(56) References Cited

U.S. PATENT DOCUMENTS 5,610,046 A 3/1997 Van Ooyen et al.

FOREIGN PATENT DOCUMENTS

WO WO 94/14965 7/1994

OTHER PUBLICATIONS

Christakopoulos et al. (1996) "Purification and characterization of two low molecular mass alkaline xylanases from Fusarium oxysporum F3" J. Biotechnol. 51:181-189.
European Search Report form Application No. EP 00 87 0028.
Georis et al. (1996) SPTREMBL Database accession No. Q59962.
Hass et al. (1992) "Purificaiton, characterization and partial amino acid sequences of a sylanase produced by penicilium chrysogenum" Biochem. Biophys. Acta, 1117(3):279-286.
Nucleotide Sequence Database EMBL, Accession No. AB035540, Dec. 18, 1999, Penicillium sp.40 xynA gene coding for xylanase A, XP002143462.
Takahashi et al. (1979) "Purification and properties of xylanase from gliocladium virens" J. Ferment Technol., 57(5):434-439.
Arase, A. et al. (1993) "Stabilization of xylanase by random mutagenesis" *FEBS* 316:123-127.
Argos, P. et al. (1979) "Thermal stability and protein structure" *Biochemistry* 18: 5678-5703.
Darnell, J. et al. (1986) "Proteins" from *Molecular Cell Biology*, Scientific American Books, Inc., New York, NY, pp. 53-54.
De Lemos Esteves, F. et al. (2005) "Improving the alkalophilic performances of the Xyl1 xylanase from *Streptomyces* sp. S38: structural comparison and mutational analysis" *Protein Sci.* 14:292-302.
Fenel, F. et al. (2004) "A de novo designed N-terminal disulphide bridge stabilizes the *Trichoderma reesei* endo-1,4-β-xylanase II" *J. Biotechnol.* 108:137-143.
Georis, J. et al. (1999) "Sequence, overproduction and purification of the family 11 endo-β-1,4-xylanase encoded by the xyl1 gene of *Streptomyces* sp. S38" *Gene* 237:123-133.
Georis, J. et al. (2000) "An additional aromatic interaction improves the thermostability and thermophilicity of a mesophilic family 11 xylanase: structural basis and molecular study" *Protein Science* 9:466-475.
Giver, L. et al. (1998) "Directed evolution of a thermostable esterase" *PNAS USA* 95:12809-12813.
Kimura, T. et al. (2000) "Purification, characterization, and molecular cloning of acidophilic xylanase from *Penicillium* sp. 40" *Biosci. Biotechnol. Biochem.* 64:1230-1237.
Kulkarni, N. et al. (1999) "Molecular and biotechnological aspects of xylanases" *FEMS Microbiology Reviews* 23: 411-456.
Olsen, M. et al. (2000) "Function-based isolation of novel enzymes from a large library" *Nature Biotechnol.* 18:1071-1074.
Olsen, M. et al. (2000) "High-throughput screening of enzyme libraries" *Curr. Opin. Biotechnol.* 11:331-337.
Payan, F. et al. (2004) "The dual nature of the wheat xylanase protein inhibitor XIP-I" *J. Biol. Chem.* 279:36029-36037.
Sali, A. et al. (1993) "Comparative protein modeling by satisfaction of spatial restraints" *J. Mol. Biol.* 234:779-815.
Shibuya, H. et al. (2000) "Enhancement of the thermostability and hydrolytic activity of xylanase by random gene shuffling" *Biochem. J.* 349:651-656.
Stemmer, W. (1994) "DNA shuffling by random fragmentation and reassembly: in vitro recombination for molecular evolution" *PNAS USA* 91:10747-10751.
Sun, J-Y et al. (2005) "Improvement of the thermostability and catalytic activity of a mesophilic family 11 xylanase by N-terminus replacement" *Protein Expression and Purification* 42: 122-130.
Torronen, A. et al. (1992) "The two major xylanases from *Trichoderma reesei*: characterization of both enzymes and genes" *Biotechnology* 10:1461-1465.
Torronen, A. et al. (1994) "Three-dimensional structure of endo-1,4-β-xylanase II from *Trichoderma reesei*: two conformational states in the active site" *The EMBO Journal* 13:2493-2501.
Torronen, A. et al. (1995) "Structural comparison of two major endo-1,4-xylanases from *Trichoderma reesei*" *Biochemistry* 34:847-856.
Torronen, A. et al. (1997) "Structural and functional properties of low molecular weight endo-1,4-β-xylanases" *J. Biotechnol.* 57:137-149.
Turunen, O. et al. (2002) "Engineering of multiple arginines into the Ser/Thr surface of *Trichoderma reesei* endo-1,4-β-xylanase II increases the thermotolerance and shifts the pH optimum towards alkaline pH" *Protein Engineering* 15:141-145.
Wakarchuk, W. et al. (1994) "Mutational and crystallographic analyses of the active site residues of the *Bacillus circulans* xylanase" *Protein Science* 3:467-475.
Wouters, J. et al. (2001) "Crystalllographic analysis of family 11 endo-β-1, 4-xylanase xyl1 from *Streptomyces* sp. s38" *Acta Cryst.* D57:1813-1819.

*Primary Examiner* — Tekchand Saidha
*Assistant Examiner* — MD. Younus Meah
(74) *Attorney, Agent, or Firm* — Knobbe, Martens, Olson & Bear, LLP

(57) ABSTRACT

The present invention is related to an isolated and purified enzyme with xylanolytic activity having more than 70% homology, preferably more than 80% homology with the amino acid sequence SEQ ID NO: 11.

31 Claims, 12 Drawing Sheets

```
                  9           18          27          36          45          54
5' GAA TTC TGC TTT GCC AAG NTT CAA CGC GGA GAC TCA CAG TCA CAT TCT TCG AAT 63          72          81          90          99         108
   CTT CTT GGC ACG TGT TCT TGG GTC CTT CGA GAA ATC ATG GAT CTG GAA AGT TAA 117         126         135         144         153         162
   CCA GTA AGC CGG TTA GAA GAC CCG GAT CAG CGA CAA ATA GCC GGT AGT AAA TTA 171         180         189         198         207         216
   CTT AAT CGT ATC GCT AGA TCT GAT CAT CCG ATA GAC AAA CAA ACA AAC TTA GGC 225         234         243         252         261         270
   TAC CCT AGA GAT GAA TCA TGA CAG TAG ACT ATT TTA CCA AGG AAT ATT TAG AAC 279         288         297         306         315         324
   AAG CAT ACC CCT CAC TAA TTG GGT TGA CTA TAT AAA TAC GGT TAA AAG CAT GGG 333         342         351         360         369         378
   GGA CTT TCC CAA GGT TGT TCC TGC CAA GCT TTG AGA TAT ACA CCC GTT GAT CCA 387         396         405         414         423         432
   TGG ATC ACC GAG GTT GTC CCT GAG CTG TCT CAA GCT TAC AAC AAC TTC CAA GGT 441         450         459         468         477         486
   TCT CCA ATG TCT TAT GAG AGC TGA TAA TCG AAA TAA GAT CAA GTA GCC GAT GTT 495         504         513         522         531         540
   TCC CCG GCT TTT AAA CTG CCT GAT CTT GGG TTT AGC CTG GCC AAG CTA CAT CCA 549         558         567         576         585         594
   TTA TAG CCG TGA TGA ATT TCC CCG CAT TTA CAC AGC CGG TGG CTG AAG TGT GCA 603         612         621         630         639         648
   ACA TGC TTA TTT TTA CTT GAA GAA GTT TAG CCG ACT CAA TAG TTT CTA CAT GCT 657         666         675         684         693         702
   TAT TTA GCT ACT AAA ATC TGA TTT TAG CCT GGT TGG ATG ATA TAG GGA TAT AGC 711         720         729         738         747         756
   TGT CGG TCC GAT GGA CCA GTA ATA GTT CAT GGA CAG TGA ACA TGA CCC GTG TTT 765         774         783         792         801         810
   AAC GTA TAA TTA GTG CAA TTG GAA CAG GGC AAG GGG ATA AAT AGG TCG TTG GCT 819         828         837         846         855         864
   AAA TTC ATT CGA GAC ATG TGG AGG ACT ATG AAA CTG TTT AAA CTC GCC CCA CAC 873         882         891         900         909         918
   CCT CCG TCA ATA TAA AAG AGG TCT TCT CCC CAA GGA ATC ATC CAT CAC AAA ACA 927         936         945         954         963         972
   CAC TCC AAT TCA TTC CTC AAT TAC CAG CAT CTG ACC TTT CAT AAT GGT CTC TTT
                                                                 M   V   S   F 981         990         999        1008        1017        1026
   CTC AAG CCT CTT TGT CGC TGC ATG CGC CGC TGT CAG TGC CCT CGC GCT TCC CAG
    S   S   L   F   V   A   A   C   A   A   V   S   A   L   A   L   P   S 1035        1044        1053        1062        1071        1080
   TGA CGT GGA AAA GCG CGA CAT CAC CCA GAA CGA GCG AGG AAC CAA CGG CGG CTA
    D   V   E   K   R   D   I   T   Q   N   E   R   G   T   N   G   G   Y 1089        1098        1107        1116        1125        1134
   CTT CTA CTC TTT CTG GAC CAA CGG TGG CGG CAG TGT CTC CTA CAA CAA CGG CAA
    F   Y   S   F   W   T   N   G   G   G   S   V   S   Y   N   N   G   N
```

FIG. 3A

```
            1143           1152           1161           1170           1179           1188
TGC AGG CCA ATA CAG TGT CAA CTG GAA GAA TTG CGG ATC TTT CAC CTC TGG CAA
 A   G   Q   Y   S   V   N   W   K   N   C   G   S   F   T   S   G   K 1197           1206           1215           1224           1233           1242
GGG CTG GGC TAC AGG TAG CGC CCG GTA AGT CCA GAC AAC ATA CTC AAT ATT GAT
 G   W   A   T   G   S   A   R /

1251           1260           1269           1278           1287           1296
AAA TAC TTA CGT CGT GTT AGA AAC ATC AAC TTT TCC GGA AAT TTC AAT CCC TCC
                         / N   I   N   F   S   G   N   F   N   P   S 1305           1314           1323           1332           1341           1350
GGA AAT GCT TAC CTG GCT GTC TAC GGC TGG ACC AAG GGC CCC CTC GTT GAG TAC
 G   N   A   Y   L   A   V   Y   G   W   T   K   G   P   L   V   E   Y 1359           1368           1377           1386           1395           1404
TAC ATC ATG GAA AAC TAT GGC GAA TAC AAC CCA GGC GGC AGC ATG ACC TTC AAG
 Y   I   M   E   N   Y   G   E   Y   N   P   G   G   S   M   T   F   K 1413           1422           1431           1440           1449           1458
GGA ACA GTA ACC AGC GAT GGG TCC GTC TAT GAT ATC TAC AAG CAT ACT CAG GTC
 G   T   V   T   S   D   G   S   V   Y   D   I   Y   K   H   T   Q   V 1467           1476           1485           1494           1503           1512
AAC CAG CCT TCG ATC ATT TCG GAT TCT AGC ACC TTC GAC CAG TAC TGG TCT ATC
 N   Q   P   S   I   I   S   D   S   S   T   F   D   Q   Y   W   S   I 1521           1530           1539           1548           1557           1566
CGT CGG AAC AAG CGT AGC AGT GGA ACT GTC ACT ACT GGT AAC CAC TTC AAT GCT
 R   R   N   K   R   S   S   G   T   V   T   T   G   N   H   F   N   A 1575           1584           1593           1602           1611           1620
TGG GCT AAG CTT GGA ATG GGT CTT GGA TCT CAC GAC TAC CAG ATT GTT AAC ACT
 W   A   K   L   G   M   G   L   G   S   H   D   Y   Q   I   V   N   T 1629           1638           1647           1656           1665           1674
GAG GGT TAC CAA AGC AGT GGA TCT GCA ACC ATC ACT GTT TCA TAA GCG TGT GAA
 E   G   Y   Q   S   S   G   S   A   T   I   T   V   S   *

1683           1692           1701           1710           1719           1728
TAC CCT GCA GTG GTT TCA TGC GAA ATG TCA CTT GCT GCT AGC AAG GGT TTG AAA 1737           1746           1755           1764           1773           1782
GAG CTA TTG TTA TGA ACC TGT TAA CTG TAT ATG GAG CAA AGT TGT GTA CCG ATA 1791           1800           1809           1818           1827           1836
CTT CAC TTC AAT CCG GTT CAT CGG GTG TTT AGC TTG TTG GTC TTC TCT TGG ATA 1845           1854           1863           1872           1881           1890
TTT GCC TTG TTA GGA ATC AAT CCA TAT TTA CGC CCC AAA TTT AAG TTT CTA GGA 1899           1908           1917           1926           1935           1944
GTA TCC ACA GGT GCT TGC CTT AGT ATG TTT CAG CCT GCG GAG TAG TAG TTT CTA 1953           1962           1971           1980           1989           1998
ACA AAA GTA ATG AGA TGC GAT GTC TAT TTT GAA AAT TGC ATG TCG CAC CTA TAT 2007           2016           2025           2034           2043           2052
GCA GAT ACT AAA AAG CAT GTC ACA AGT GGC TAT ATA TCG ACA ATA GTG GTT AGT 2061           2070           2079           2088           2097           2106
ATA TCA CCG TTC CTA AAA GTG CAT TTC GCA TAA CTC ACA TTC TGT TGG GGA TCA 2115           2124           2133           2142           2151           2160
GTG AAA CCA CAA CTA GGC CCA CTA CTT TTC TTC GGT ATC TTC CCG AAC TTC TTA 2169           2178           2187           2196           2205           2214
CGC CCG CTA AGC GGC GCC TTG TGC GCC AAC GGA TAC CCA TAC CAA AAC CAC CAA

2223
CTT GGG GGG GA 3'
```

FIG. 3B

```
              10        20        30        40        50        60
         ....*....|....*....|....*....|....*....|....*....|....*....|
consensus    1 AGGYYYSNWTDGGGTVTYLNSGGGSFSVQWS--NIGNFVVGKGWTTGS--------GNIV  50
1XNB         1 ASTDYWQNWTDGGGIVNAVNGSGGNYSVNWS--NTGNFVVGKGWTTGS--------PFRT  50
1XYP A      10 MNGYFYSYWNDGHGGVTYTNGPGGQFSVNWS--NSGNFVGGKGWQPGT--------KNKV  59
1XYN         1 ASINYDQNYQ-TGGQVSYSPS-NTGFSVNWN--TQDDFVVGVGWTTGS--------SAP   47
1BK1         2 AGINYVQNYNGNLGDFTYDES-AGTFSMYWEdgVSSDFVVGLGWTTGS--------SNA   51
gi 139885   60 tDGMYYSFWTDGGGSVSMTLNGGGSYSTQWT--NCGNFVAGKGWSTGD--------GN--  107
gi 549462   10 DGGYYYSWWTDGAGDATYQNNGGGSYTLTWSg-NNGNLVGGKGWNPGA--------ASRS  60
gi 731173   40 HNGCFWSWWSDGGARATYTNGAGGSYSVSWG--SGGNLVGGKGWNPGT--------A-RT  88
gi 139875   38 VGGYDYEMWNQNGQGQASMNPGAGSFTCSWS--NIENFLARMGKNYDSqkknykafGNIV  95
gi 1351448  42 HGGYDYELWKDYGNTIMELND-GGTFSCQWS--NIGNALFRKGRKFNSdkty-qelGDIV  97
gi 139871   70 NGGYDYELWKDYGNTSMLKN-GGAFSCQWS--NIGNALFRKGKKFNDtqty-kqlGNIS  125

70        80        90       100       110       120
         ....*....|....*....|....*....|....*....|....*....|....*....|
consensus   51 INYSGSYN-PNGNSYLCVYGWTRNPLVEYYIVENWGTYRPTGT-ATKkgTVTSDGGTYDI 108
1XNB        51 INYNAGVWaPNGNGYLTLYGWTRSPLIEYYVVDSWGTYRPTGT-YKG--TVKSDGGTYDI 107
1XYP A      60 INFSGSYN-PNGNSYLSVYGWSRNPLIEYYIVENFGTYNPSTG-ATKlgEVTSDGSVYDI 117
1XYN        48 INFGGSFSvNSGTGLLSVYGWSTNPLVEYYIMEDNHNYP--AQ-GTVkgTVTSDGATYTI 104
1BK1        52 ITYSAEYSaSGSSSYLAVYGWVNYPQAEYYIVEDYGDYNPCSS-ATSlgTVYSDGSTYQV 110
gi 139885  108 VRYNGYFN-PVGNGYGCLYGWTSNPLVEYYIVDNWGSYRPTGT-YKG--TVSSDGGTYDI 163
gi 549462   61 ISYSGTYQ-PNGNSYLVYGWTRSSLIEYYIVESYGSYDPSSA-ASHkgSVTCNGATYDI 118
gi 731173   89 ITYSGTYN-YNGNSYLAVYGWTRNPLVEYYVVENFGTYDPSSQ-SQNkgTVTSDGSSYKI 146
gi 139875   96 LTYDVEYT-PRGNSYMCVYGWTRNPLMEYYIVEGWGDWRPPGNdGEVkgTVSANGNTYDI 154
gi 1351448  98 VEYGCDYN-PNGNSYLCVYGWTRNPLVEYYIVESWGSWRPPGA-TPKgtITQWMAGTYEI 155
gi 139871  126 VNYDCNYQ-PYGNSYLCVYGWTSSPLVEYYIVDSWGSWRPPGG-TSKgtITVDGG-IYDI 182

130       140       150       160       170       180
         ....*....|....*....|....*....|....*....|....*....|....*....|
consensus  109 YETTRVNQPSIDG-TATFQQYWSVRQSKRTSG-------GTVTVTNHFDAWASLGMNLG- 159
1XNB       108 YTTTRYNAPSIDGdRTTFTQYWSVRQSKRPTGs-----nATITFTNHVNAWKSHGMNLGs 162
1XYP A     118 YRTQRVNQPSIIG-TATFYQYWSVRRNHRSs--------GSVNTANHFNAWAQQGLTLG- 167
1XYN       105 WENTRVNEPSIQG-TATFNQYISVRNSPRTSG--------TVTVQNHFNAWASLGLHLG- 154
1BK1       111 CTDTRTNEPSITG-TSTFTQYFSVRESTRTSG--------TVTVANHFNFWAQHGFGNS- 160
gi 139885  164 YQTTRYNAPSVEG-TKTFQQYWSVRQSKVTSGs------GTITTGNHFDAWARAGMNMGq 216
gi 549462  119 LSTWRYNAPSIDG-TQTFEQFWSVRNPKKAPGgs---isGTVDVQCHFDAWKGLGMNLGs 174
gi 731173  147 AQSTRYNQPSIDG-TRTFQQYWSVRQNKRSs--------GSVNMKTHFDAWASKGMNLG- 196
gi 139875  155 RKTMRYNQPSLDG-TATFPQYWSVRQTSGSANnqtnymkGTIDVTKHFDAWSAAGLDMSg 213
gi 1351448 156 YETTRVNQPSIDG-TATFQQYWSVRTSKRTSG--------TISVTEHFKQWERMGMRMG- 205
gi 139871  183 YETTRINQPSIQG-NTTFKQYWSVRRTKRTSG--------TISVSKHFAAWESKGMPLG- 232

190       200
         ....*....|....*....|..
consensus  160 KMYYQIVAVEGYQSSGSANVTV  181
1XNB       163 NWAYQVMATEGYQSSGSSNVTV  184
1XYP A     168 TMDYQIVAVEGYFSSGSASITV  189
1XYN       155 QMNYQVVAVEGWGGSGSASQSV  176
1BK1       161 DFNYQVMAVEAWSGAGSASVTI  182
gi 139885  217 FRYYMIMATEGYQSSGSSNITV  238
gi 549462  175 EHNYQIVATEGYQSSGTATITV  196
gi 731173  197 QHYYQIVATEGYFSTGNAQITV  218
gi 139875  214 TLYEVSLNIEGYRSNGSANVKS  235
gi 1351448 206 KMYEVALTVEGYQSSGYANVYK  227
gi 139871  233 KMHETAFNIEGYQSSGKADVNS  254
```

*Figure 6*

```
M1P     MVSFSSLFVAACAAVSALALPSDVEKRDITQNERGTNGGYFYSFWTNGGGSVSYNNGNGG  60
M2P     MVSFSSLFVAACAAVSALALPSDVEKRDITQNERGTNGGYFYSFWTNGGGSVSYNNGNGG  60
M3P     MVSFSSLFVAACAAVSALALPSDVEKRDITQNERGTNGGYFYSFWTNGGGSVSYNNGNNG  60
WT      MVSFSSLFVAACAAVSALALPSDVEKRDITQNERGTNGGYFYSFWTNGGGSVSYNNGNAG  60
        ************************************************************ *

M1P     QYSVNWKNCGSFTSGKGWQPGKNKVINFSGNFNPSGNAYLAVYGWTKGPLVEYYIMENYG 120
M2P     QYSVNWKNCGSFTSGKGWQPGKNKVINFSGNFNPSGNAYLAVYGWTKGPLVEYYIMENYG 120
M3P     QYSVNWSNCGNFTSGKGWQPGKRKDINFSGNFNPSGNAYLAVYGWTKGPLVEYYIMENYG 120
WT      QYSVNWKNCGSFTSGKGWATGSARNINFSGNFNPSGNAYLAVYGWTKGPLVEYYIMENYG 120
        ******.***.******  .*. : ***********************************

M1P     TYNPGGGATKLGEVTSDGSVYDIYKHTQVNQPSIISDTATFDQYWSVRRNHRSSGTVTTG 180
M2P     TYNPGGGASKLGELTTDGAVYDIYKHTQVNQPSIIGDTATFDQYWSVRRNHRSSGTVTTG 180
M3P     DYNPGGGATKLGEVNTDGGTYDIYKHTQVNQPSIIGDTKTFDQYWSVRQSHRSSGTVTTG 180
WT      EYNPGGSMTFKGTVTSDGSVYDIYKHTQVNQPSIISDSSTFDQYWSIRRNKRSSGTVTTG 180
         ****.  :  * :.:**..*************.*: *******:*:..:*********

M1P     NHFNAWAKQGLGLGTHDYQIVNTEGYFSSGSATITVS 217        (SEQ ID NO :15)
M2P     NHFNAWAKQGLGMGTHDYQIVNTEGYFSSGSATITVS 217        (SEQ ID NO :16)
M3P     NHFNAWAKQGLGLGTHDYQIVNTEGYESSGSATITVS 217        (SEQ ID NO :17)
WT      NHFNAWAKLGMGLGSHDYQIVNTEGYQSSGSATITVS 217        (SEQ ID NO :11)
        ******** *.*.*:*********** *********
```

*Figure 8*

MVSFSSLFVAACAAVSALALPSDVEKRDITQNERGTNGGYFYSFWTNGGGSVSYNNG
NX$_1$GQYSVNWX$_2$X$_3$CGX$_4$FTSGKGWX$_5$X$_6$GX$_7$X$_8$X$_9$X$_{10}$INFSGNFNPSGNAYLAVYGWTK
GPLVEYYIMENYGX$_{11}$YNPGGX$_{12}$X$_{13}$X$_{14}$X$_{15}$X$_{16}$GX$_{17}$X$_{18}$X$_{19}$X$_{20}$DGX$_{21}$X$_{22}$YDIYKHTQ
VNQPSIIX$_{23}$DX$_{24}$X$_{25}$TFDQYWSX$_{26}$RX$_{27}$X$_{28}$X$_{29}$X$_{30}$X$_{31}$X$_{32}$GTVTTGNHFNAWAKX$_{33}$G
X$_{34}$GX$_{35}$GX$_{36}$HDYQIVNTEGYX$_{37}$SSGSATITVS     (SEQ ID NO:18)

ENZYME WITH XYLANASE ACTIVITY

RELATED APPLICATIONS

This is a continuation-in-part of U.S. patent application Ser. No. 11/153,260, filed on Jun. 15, 2005 now abandoned, which is a continuation of U.S. patent application Ser. No. 09/790,070, filed on Feb. 21, 2001, now abandoned, which claims priority to European Patent Application 00870028.8, filed on Feb. 21, 2000, all of which are hereby incorporated by reference.

FIELD OF THE INVENTION

The present invention relates to an enzyme with xylanase activity identified by its amino acid and nucleotide sequences and variants thereof.

The present invention relates also to their uses in the agrofood and in the pulp and paper industries.

BACKGROUND OF THE INVENTION

Xylans are heteropolysaccharides which form the major part of the hemicellulose present in the plant biomass.

The backbone of these polysaccharides is a chain of β-1,4 linked xylopyranosyl residues. Many different side groups could bind to these residues like acetyl, arabinosyl and glucuronosyl residues. Phenolic compounds such as ferulic or hydroxycinnamic acids are also involved through ester binding in the cross linking of the xylan chains or in the linkage between xylan and lignin chains for example.

Endoxylanases hydrolyze specifically the backbone of the hemicellulose. In some cases, the side groups may mask the main chain by steric hindrance. Different xylanase activities already described are characterized by their specificity towards their substrate and the length of the oligomers produced.

These differences between the xylanases concerning their properties seem to be partly related to their respective amino acid sequences. Endoxylanases have been classified into two families (F or 10 and G or 11) according to their sequence similarities (Henrissat & Bairoch 1993) *Biochem. J.* 293: 781). The F family of xylanases are larger, more complex as compared to the G family of xylanases. Moreover the F family xylanases produce small oligosaccharides, while the G family xylanases show a higher affinity for unsubstituted xylan.

Xylanases are used in various industrial areas such as the pulp, paper, feed and bakery industries. Other applications include the juice and beer industries. Xylanases could also be used in the wheat separation process. The observed technological effects are, among others, improved bleachability of the pulp, decreased viscosity of the feed or changes in dough characteristics.

Many different microbial genera have been described to produce one or several xylanases. These microbial genera comprise bacteria as well as eukaryotic organisms like yeast or fungi.

SUMMARY OF THE INVENTION

The present invention relates to providing an isolated and purified enzyme with xylanase activity.

Another aspect of the present invention provides a method for using the enzyme with xylanase activity in different kinds of industries such as agrofood, pulp, paper industries.

BRIEF DESCRIPTION OF THE DRAWINGS

FIGS. 3 A and B represents the complete genetic sequence of the xylanase according to the invention (SEQ ID NO: 8).

FIG. 6 shows the alignment of ten representative Family G/11 xylanase amino acid sequences available before the priority date of the present application: 1XNB Xylanase (Endo-1,4-Beta-Xylanase) (E.C.3.2.1.8) of *Bacillus circulans* (SEQ ID NO: 20; 1XYP_A Chain A, Molecule: Endo-1,4-Beta-Xylanase Ii; Synonym: Xynii; Ec: 3.2.1.8 of *Trichoderma reesei* (SEQ ID NO: 21); 1XYN Endo-1,4-Beta-Xylanase I; Synonym: Xyni; Ec: 3.2.1.8. of *Trichoderma reesei* (SEQ ID NO: 22); 1BK1 Endo-1,4-Beta-Xylanase C of *Aspergillus kawachii* (SEQ ID NO: 23); gi 139885 Endo-1, 4-beta-xylanase C precursor (Xylanase C) (1,4-beta-D-xylan xylanohydrolase C) of *Streptomyces lividans* (SEQ ID NO: 24); gi 549462 Endo-1,4-beta-xylanase A (Xylanase A) (1,4-beta-D-xylan xylanohydrolase A) of *Schizophyllum commune* (SEQ ID NO: 25); gi 731173 Endo-1,4-beta-xylanase I precursor (Xylanase I) (1,4-beta-D-xylan xylanohydrolase 1) of *Cochliobolus carbone* (SEQ ID NO: 26); gi 139875 Bifunctional endo-1,4-beta-xylanase xylA precursor of *Ruminococcus flavefaciens* (SEQ ID NO: 27); gi 1351448 Endo-1,4-beta-xylanase A precursor (Xylanase A) (1,4-beta-D-xylan xylanohydrolase A) of *Clostridium stercorarium* (SEQ ID NO: 28); gi 139871 Endo-1,4-beta-xylanase precursor (Xylanase) (1,4-beta-D-xylan xylanohydrolase) of *Clostridium saccharobutylicum* (SEQ ID NO: 29). The consensus sequence is SEQ ID NO: 19. Uppercase—aligned residues; lowercase—non-aligned residues; italics—unaligned residues and columns not fully covered by all sequences; normal font and bold font—conserved columns.

FIG. 8 represents a multiple sequence alignment of M1P (SEQ ID NO: 15), M2P (SEQ ID NO: 16) and M3P (SEQ ID NO: 17) with the wild-type (WT) *P. griseofulvum* xylanase sequence (SEQ ID NO: 11).

FIG. 11 represents SEQ ID NO: 18. X1: A, G or N; X2: K, S, T, V, Q, E, A or R; X3: N or D; X4: S or N; X5: A, Q, N or S; X6: T, P or N; X7: S, K, N, A or G; X8: A, N, R, T or S; X9: R, K, Q, H or R; X10: N, V, D, T or A; X11: E, T, D or S; X12: S or G; X13: M, A, L or G; X14: T, S, Q or E; X15: F, K or Y; X16: K, L, R or M; X17: T, E, Q or S; X18: V, L or F; X19: T, Q, E, N or possibly Y or K; X20: S or T; X21: S, A or G; X22: V or T; X23: S or G; X24: S or T; X25: S, A, K or R; X26: I or V; X27: R, T or Q; X28: N, S, E or Q; X29: K or H; X30:

Figure 1:
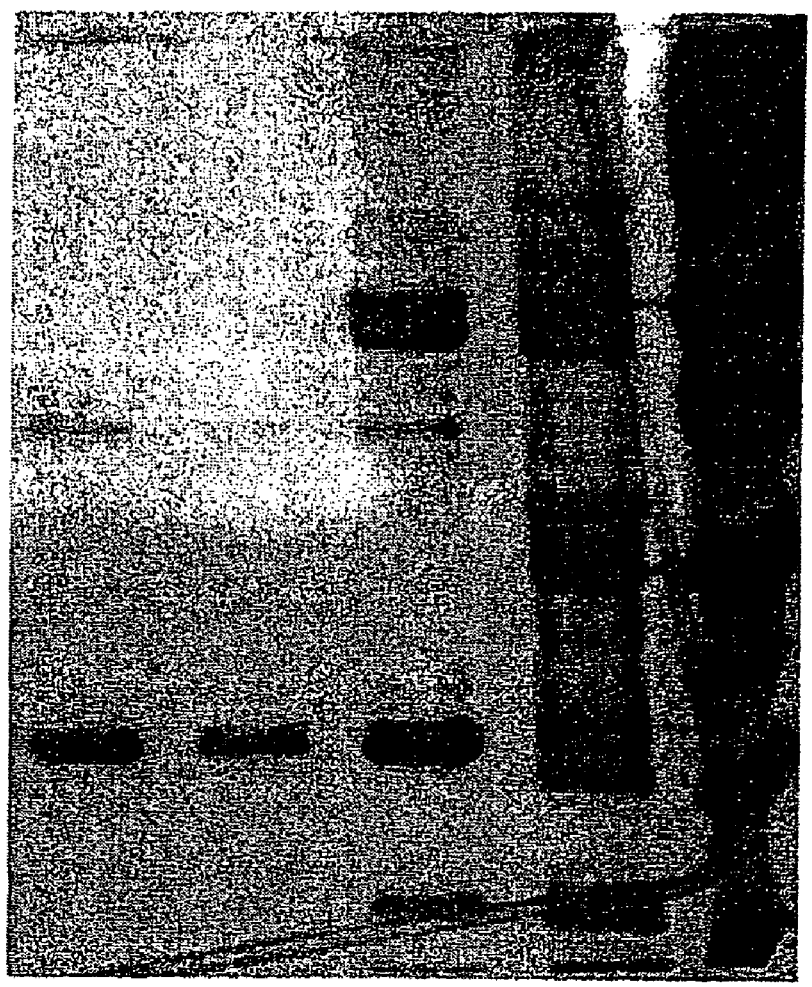
FIG. 1 shows a SDS-polyacrylamide gel of the proteins recovered after the successive purification steps of the enzyme with xylanolytic activity.

R or V; X31: S, T or V; X32: S or G; X33: L, Q, Y or H; X34: M or L; X35: L or M; X 36: S, T or N; X37: Q, F, K or E.

DETAILED DESCRIPTION OF THE PREFERRED EMBODIMENT

A first aspect of the present invention is related to an isolated and purified (from possible contaminants) xylanase amino acid sequence presenting more than 50%, preferably more than 70, 75, 80, 82, 85 or 87%, more preferably more than 90, 95, 97 or 99% homology (or sequence identity) with the amino acid sequence SEQ ID NO: 11.

Advantageously, the isolated and purified xylanase amino acid sequence according to the invention has a molecular weight comprised between 22 kD and 26 kD, preferably a molecular weight approximately 24 kD. The size of the mature protein is on average comprised between 20 and 21 kDa, more preferably is about 20.5 kDa.

Said xylanase amino acid sequence or peptide is expressed extracellularly or intracellularly and/or secreted by the recombinant host cell according to the invention.

According to another preferred embodiment of the present invention, the isolated and purified xylanase amino acid sequence has the amino acid sequence of SEQ ID NO: 11 or a smaller portion of said amino acid sequence (of more than 30 or 50 amino acids, preferably more than 100, 120, 150, or 170 amino acids, most preferably more than 185, 195, 200, 205, 210 or 215 amino acids), which has at least more than 80, 85 or 90% of the xylanase activity of the complete amino acid sequence SEQ ID NO: 11, preferably more than 95% of the xylanase activity or the complete xylanase activity of the complete amino acid sequence SEQ ID NO: 11 (see also Example 1). In other words, the isolated and purified xylanase amino acid sequence according to the invention may be deleted partially while maintaining its enzymatic activity, which may be measured by methods well known by persons skilled in the art. For instance, the first 8 amino acid of SEQ ID NO: 11 may be deleted. A preferred embodiment of the present invention relates to an isolated or purified enzyme comprising SEQ ID NO: 11, a homologue with more than 70% homology (sequence identity) with the amino acid sequence SEQ ID NO: 11, or a portion thereof.

The purified xylanase enzyme according to the invention is also characterized by an optimum pH around pH 5.0 and temperature profile having its maximum activity at about 50° C. More generally, the maximum activity of the enzyme is between pH 4.5 and 7.0, at a temperature comprised 35° C. and 55° C. (see FIG. 4).

The present invention is also related to an isolated and purified nucleotide sequence from a microorganism, encoding a xylanase. Preferably, said microorganism is selected from the group consisting of bacteria or fungi (including yeast), preferably the *Penicillium* species fungi, more specifically *Penicillium griseofulvum*.

According to a preferred embodiment of the present invention, said microorganism is *Penicillium griseofulvum* having the deposit number MUCL-41920.

According to the invention, said nucleotide sequence presents more than 50%, preferably more than 70, 75, 80 or 85%, more preferably more than 87, 90 or 95% homology (or sequence identity) with the sequence SEQ ID NO: 8 described hereafter.

According to a preferred embodiment of the present invention, said isolated and purified nucleotide sequence corresponds to the nucleotide sequence SEQ ID NO: 8 or a portion thereof encoding a peptide having a xylanase activity.

It is meant by "a portion of the nucleotide sequence SEQ ID NO: 8", a fragment of said sequence SEQ ID NO: 8 having more than 90 nucleotides, preferably more than 100 nucleotides or more than 120 nucleotides, of said nucleotide sequence and encoding a protein characterized by a xylanase enzymatic activity similar to the xylanase activity of the complete amino acid sequence SEQ ID NO: 11. Preferably, said portion has a xylanase enzymatic activity of more than 80% of the initial xylanase enzymatic activity of the complete enzyme defined by its amino acid sequence SEQ ID NO: 11, preferably has a xylanase enzymatic activity corresponding to the one of amino acid sequence SEQ ID NO: 11. Said portion may have 300, 360, 450, or 510 (consecutive) nucleotides of SEQ ID NO: 8, or preferably more than 555, 585, 600, 615, 630 or more than 645 (consecutive) nucleotides of SEQ ID NO: 8.

Another aspect of the present invention is related to a recombinant nucleotide sequence comprising, operably linked to the nucleotide sequence according to the invention and above-described, one or more adjacent regulatory sequence(s), preferably originating from homologous microorganisms. However, said adjacent regulatory sequences may also be originating from heterologous microorganisms. These adjacent regulatory sequences are specific sequences such as promoters, secretion signal sequences and terminators.

Another aspect of the present invention is related to the vector comprising the nucleotide sequence(s) according to the invention, possibly operably linked to one or more adjacent regulatory sequence(s) originating from homologous or from heterologous microorganisms.

It is meant by "a vector", any biochemical construct which may be used for the introduction of a nucleotide sequence (by transduction, transfection, transformation, infection, conjugation, etc.) into a cell. Advantageously, the vector according to the invention is selected from the group consisting of plasmids, viruses, phagemids, chromosomes, transposons, liposomes, cationic vesicles or a mixture thereof. Said vector may comprise already one or more of the above-described adjacent regulatory sequence(s) (able to allow its expression and its transcription into a corresponding peptide by said microorganism). Preferably, said vector is a plasmid incorporated into *E. coli* and having the deposit number LMBP-3987.

The present invention is also related to the host cell, preferably a recombinant host cell, "transformed" by the nucleotide sequence or the vector according to the invention above-described.

It is meant by "a host cell "transformed" by the nucleotide sequence or the vector according to the invention", a cell having incorporated said nucleotide sequence or said vector and which does not comprise naturally (originally) said nucleotide sequence. The transformed host cell may also comprise a cell having incorporated said vector or said nucleotide sequence by genetic transformation, preferably by homologous recombination or other method (recombinant microorganism).

A "host cell" may be also the original cell comprising the nucleotide sequence encoding the enzyme according to the invention and genetically modified (recombinant host cell) to overexpress or express more efficiently said enzyme (better pH profile, higher extracellular expression, etc.).

Preferably, said host cell is also capable of overexpressing (higher expression than the expression observed in the initial microorganism) said nucleotide sequence or said vector and allows advantageously a high production of an amino acid sequence encoded by said nucleotide sequence or by said vector. The isolated and purified nucleotide sequence according to the invention may be either integrated into the genome of the selected host cell or present on an episomal vector in said host cell.

Advantageously, the recombinant host cell according to the invention is selected from the group consisting of the microbial world, preferably bacteria or fungi (including yeast).

Preferably, said recombinant host cell is modified to obtain an expression of the xylanase enzyme at a high level, obtained by the use of adjacent regulatory sequences being capable of directing the overexpression of the nucleotide sequence according to the invention in the recombinant host cell or by increasing the number of nucleotide copies of the sequences according to the invention.

The following description describes also the conditions (culture media, temperature, pH conditions, etc.) for the culture of the host selected for the expression of the xylanase according to the invention. For this purpose, the original production species and/or a suitable host cell transformed with a DNA construct designed to express the said enzyme are present in a suitable growth medium.

According to the present invention, said protein with xylanolytic activity may be isolated from the medium and/or purified. The culture, isolation and purification conditions are derived from conventional methods well-known to persons skilled in the art.

The xylanase enzyme according to the invention may be used in different kinds of industries.

The enzyme with xylanolytic activity of the present invention, purified or not purified, is particularly suited as a bread-improving agent. Bread-improving agents are products which could improve or increase texture, flavor, anti-staling effect, softness, crumb softness upon storage, freshness and machinability, volume of a dough and/or of a final baked product. Preferably, said enzyme with xylanolytic activity increases the specific volume of the final baked product.

"Baked product" intends to include any product prepared from dough, in particular a bread product. Dough is obtained from any type of flour or meal (for example, based on rye, barley, oat or maize), preferably prepared with wheat or with mixes including wheat.

A further aspect of the present invention relates to the additive effect of said enzyme having xylanolytic activity with other enzymes, in particular with an alpha-amylase, preferably an alpha-amylase from *Aspergillus oryzae*. Said enzyme with xylanolytic activity may be used in combination with other bread-improving agents like enzymes, emulsifiers, oxidants, milk powder, fats, sugars, amino acids, salts, or proteins (gluten, cellulose binding site) well known to persons skilled in the art.

According to the present invention, the enzyme with xylanolytic activity, purified or not, shows hydrolytic activities in presence of plant cell wall components. Particularly, said enzyme degrades the wheat cell wall components. Particularly, the degradation activities lead to a decrease of the flour viscosity in the presence of water. Said enzyme may thus advantageously be used in the separation of components of plant cell materials such as cereal components. Particularly, said enzyme may be used to improve the separation of the wheat into gluten and starch by the so-called batter process.

According to the present invention, said enzyme may be used to improve the filtrability and/or decrease the viscosity of glucose syrups obtained from impure cereal starch by subjecting the impure starch first to the action of an alpha-amylase, then to the action of said xylanase. It may also be used in beer brewing when cereal has to be degraded to improve the filtrability of the wort or to reuse the residuals from beer production for example, animal feed. Said enzyme may be used in feed to improve the growth rate or the feed conversion ratio of animals such as poultry.

Another application resides in the oil extraction where oil has to be extracted from the plant material such as the corn oil from corn embryos. The enzyme with xylanolytic activity of the present invention may be used in fruit and vegetable juice processing to improve the yield. According to the present invention, said enzyme may be used in all processes involving plant materials or waste materials, for example, from paper production, or agricultural wastes such as wheat-straw, corn cobs, whole corn plants, nut shells, grass, vegetable hulls, bean hulls, spent grains, sugar beet, and the like.

The effect of the enzyme with xylanolytic activity of the present invention may be further improved by adding other enzymes in combination with said enzyme. Such enzymes may belong, but are not restricted to, hydrolytic enzymes families such as glucanases, proteases, cellulases, hemicellulases, or pectinases. Other enzymes are transglutaminases, oxido-reductases and isomerases, etc.

The enzyme with xylanolytic activity according to the invention may be used under several forms. Cells expressing the enzyme, such as yeast, fungi, archaea or bacteria, may be used directly in the process. Said enzyme may be used as a cell extract, a cell-free extract (i.e. portions of the host cell that have been submitted to one or more disruption, centrifugation and/or extraction steps) or as a purified protein. Any of the above-described forms may be used in combination with one or more other enzyme(s) under any of the above-described forms. These whole cells, cell extracts, cell-free extracts or purified enzymes may be immobilized by any conventional means on a solid support to allow protection of the enzyme, continuous hydrolysis of substrate and/or recycling of the enzymatic preparation. Said cells, cell extracts, cell-free extracts or enzymes may be mixed with different ingredients (such as in the form of a dry power or a granulate, in particular a nondusting granulate, in a form of a liquid, for example with stabilizers such as polyols, sugars, organic acids, sugar alcohols according to well-established methods).

A further aspect of the present invention relates to isolated or purified xylanase enzymes comprising (or consisting of) a xylanase sequence, preferably a family 11 (formerly G) xylanase sequence, having more than 70%, 75%, yet more preferably more than 80, 82, 85, 87, 90% or even more than 95% sequence identity (over the entire length) with the amino acid sequence of SEQ ID NO: 11. These variant or mutant forms of SEQ ID NO: 11 advantageously exhibit xylanolytic activity. Said variants differ in at least 1, 2, 3, 4, 5, 6, 7, 8, 9, 10, 15, 20, 25, 30, 35, 40, 45, 50, 55, 60 amino acids from SEQ ID NO: 11.

Preferably the N-terminal part of SEQ ID NO: 11 and the first 30 residues of the mature enzyme are maintained (i.e. not modified, deleted or substituted). The first 8 amino acids of SEQ ID NO: 11 may, however, be deleted. Advantageously, the Ser44 of the mature enzyme is maintained as well as the catalytic site residues, the three putative CK2-Phospho sites (residues 3-6, 112-115, 132-135), the nine putative myristyl N-myristoylation sites, a putative N-glycosilation site (residues 60-63) and a putative CAMP-Phospho site (residues 144-147). The positions recited here are those in the mature enzyme.

The present invention relates amongst others to variant and mutant sequences with single or multiple modifications (preferably amino acid substitutions) compared to SEQ ID NO: 11. The invention in particular relates to variants of SEQ ID NO: 11 with one or more modifications (amino acid substitutions) at one or more of the following positions: 32, 40, 41, 44, 52, 53, 55, 56, 57, 58, 94, 100, 101, 102, 103, 104, 106, 107, 108, 109, 112, 113, 129, 131, 132, 140, 142, 143, 144, 145, 146, 147, 162, 164, 166, 168 or 180. Particular examples of such variants are xylanase sequences having or comprising the amino acid sequence of SEQ ID NO: 15, SEQ ID NO: 16 or SEQ ID NO: 17. Such modifications advantageously do not affect the structure and thereby the functionality and function of the xylanase of the invention. The positions recited here are those in the mature enzyme. By "at least one" is meant that at least, 1, 2, 3, 4, 5, 6, 7, 8, 9, 10, 11, 12, 13, 14, 15, 16, 17, 18, 19, 20, 21, 23, 24, 25, 26, 27, 28, 29, 30, 31, 32, 33, 34, 35, 36, possibly all of the above amino acids at the above positions are substituted (modified). Preferred substituents are given in Tables 5-7.

Preferred mutant sequences according to the invention comprise at least one or more of the following substitutions:

A32G,N (meaning that A at position 32 may be replaced by G or N)
K40S, T, V, Q, E, A, R
N41D
S44N
A52Q,N,S
T53P,N
S55K,N,A,G
A56N,R,T,S
R57K,Q,H,R
N58V,D,T,A
E94T,D,S
S100G
M101A,L,G
T102S,Q,E
F103K,Y
K104L,R,M
T106E,Q,S
V107L,F
T108Q,E,N,(Y,K) ( ) meaning that Y and K are less plausible
S109T
S112A,G
V113T
S129G
S131T
S132A,K,R
I140V
R142T,Q
N143S,E,Q
K144H
R145V
S146T,V
S147G
L162Q,Y,A,H
M164L
L166M
S168T,N
Q180F,K,E.

A possible mutant according to the invention is one comprising or having (consisting of) the amino acid sequence SEQ ID NO: 18.

The invention will be described in further detail in the following examples by reference to the enclosed drawings, without limiting its scope.

EXAMPLE 1

Purification of an Enzyme with Xylanolytic Activity from *Penicillium griseofulvum* A160 Strain 5 g of a commercial Belgian wheat flour were suspended in 50 ml saline solution (NaCl 0.9%). Aliquots of 100 µl of this suspension were spread on AMAM plates (*Aspergillus* Minimum Agar Medium: glucose 1%, NaNO$_3$ 0.6%, KCl 7 mM, Kh$_2$PO$_4$ 11 mM, MgSO$_4$ 2 mM, ZnSO$_4$ 76 µM, H$_3$BO$_3$ 178 µM, MnCl$_2$ 25 µM, FeSO$_4$ 18 µM, CoCl$_2$ 7.1, µM CuSO$_4$, 6.4 µM, Na$_2$MoO$_4$ 6.2 µM, EDTA 174 µM, pH 6.5 (Pontecorvo et al. 1953 *Adv. Genet.* 5:142) supplemented with 1.5% bacto-agar and 100 µg/ml ampicilline.

Among the strains that appeared on the plates after incubation at 30° C., a particular strain was isolated and identified as *Penicillium griseofulvum* with the isolation reference A160 (MUCL-41920).

Determination of the Xylanolytic Activity

The xylanolytic activity was determined by measuring the reducing sugars formed from the Beechwood xylan (Sigma). The reducing sugars were revealed with the 2,3-dinitrosalicylic acid (Bailey et al. 1992 *J. Biotechnol.* 23:257). The reaction was carried out by 30° C. in a 100 mM acetate buffer at pH 4.5. The xylanolytic activity was expressed in µmole xylose/min.

For rapid identification of the enzyme, the xylanolytic activity was assayed using Azo-xylan (Megazyme) as substrate following the supplier instructions with the exception that the reaction was carried out at 35° C. in a 100 mM citrate-phosphate buffer at pH 6.0.

In this case, one xylanase unit was arbitrarily defined as the amount of enzyme required to increase the optical density by one unit at 595 nm in 10 min.

Purification of the Xylanolytic Enzyme

The strain of *Penicillium griseofulvum* A160 was cultivated in 2 liters of *Aspergillus* Minimal Medium pH 6.5 (Pontecorvo et al. 1953 *Adv. Genet.* 5:142), supplemented with 1% xylan from oat spelt (Sigma) at 30° C. After 72 hours, the culture was filtered through a Miracloth filter (Calbiochem) to remove the mycelium. The filtrate was concentrated by ultrafiltration in a Pellicon device with a 10 kDa Biomax 10 cassette (Millipore) to a final volume of 170 ml. The concentrate was diluted 3 times to reach a final concentration of 50 mM in sodium acetate pH 4.2.

This solution was loaded at 2 ml/min on a Pharmacia XK16/20 column filled with 30 ml of the Bio-Rad Macro High S resin equilibrated in 50 mM sodium acetate pH 4.2. Proteins were eluted with a linear increasing NaCl gradient from 0 M to 0.6 M in 50 mM sodium acetate pH 4.2. Xylanase activity was determined in the eluted fractions. Active fractions were pooled and equilibrated in 1.2 M ammonium sulfate, 50 mM sodium acetate pH 5.0 in a final volume of 65 ml.

These were applied on a Phenyl Sepharose HP column (Pharmacia) and eluted at 2.5 ml/min with a 1.2 M to 0 M ammonium sulfate linear gradient in a 50 mM sodium acetate pH 5.0 buffer. Xylanase activity was determined in the eluted fractions. The xylanase activity was collected as one peak at 0.8 M ammonium sulfate.

One major protein is present in this peak as shown by SDS-polyacrylamide gel (FIG. 1).

EXAMPLE 2

Determination of the Amino Acid Sequence of the Enzyme with Xylanolytic Activity General procedures were followed to perform the N-terminal sequencing of the protein after electrophoresis on a 12% SDS-polyacrylamide gel and electroblotting on a PVDF Immobilon-P membrane (Millipore). An automated 477A Protein Sequencer coupled to a HPLC 120A Analyzer (Applied Biosystems) was used.

The following sequence has been obtained with the protein with an apparent molecular weight of 24 kDa:

SEQ ID NO 1:
D I T Q N E R G T N N G Y F Y S F W T X G G G N
V Y

EXAMPLE 3

Cloning of a Gene Coding for a Enzyme with Xylanolytic Activity

Cloning of Internal DNA Fragments

The genomic DNA from *Penicillium griseofulvum* A160 was isolated according to Boel et al. (1984 *EMBO J.* 7:1581). The strain was grown in 50 ml *Aspergillus* Minimum Medium supplemented with 0.5% Yeast Extract (Difco). After 24 hours, the mycelium was harvested by filtration on a Miracloth filter and washed twice with water. 1 g mycelium was incubated in 10 ml solution A (sorbitol 1 M, EDTA 25 mM, pH 8.0) for 30 min at 30° C. The cells were then centrifuged and suspended in 10 ml solution B (Novozym 234 20 mg, sorbitol 1 M, sodium citrate 0.1 M, EDTA 10 mM, pH 5.8). After 30 min at 30° C., the cells were centrifuged and lysed with 15 ml of solution C (phenol 40%, SDS 1%). DNA was separated from the contaminating material by successive extractions with phenol and phenol-chloroform, followed by ethanol precipitation.

The degenerate synthetic oligonucleotides mixtures SEQ ID NO: 2 and SEQ ID NO: 3 were designed based on the N-terminal sequence. A third synthetic oligonucleotides mixture SEQ ID NO: 4 has been designed based on a hypothetical degenerate sequence coding for the amino acid sequence EYYIVD (SEQ ID NO: 14), conserved among the family G xylanases.

SEQ ID NO: 2:
GGY TAY TTY TAY AAY TTY TGG AC

SEQ ID NO: 3:
GGY TAY TAY TAY TCI TTY TGG AC

SEQ ID NO 4:
TCG ACR AYG TAG TAY TC

In these sequences, Y stands for T or C, R for A or G, I for inosine.

The PCR reaction was carried out with 10 ng gDNA of *Penicillium* griseofulvum A160 in the presence of 5 pmole of each synthetic oligonucleotides mixture SEQ ID NO: 2 and SEQ ID NO: 3 and 10 pmole synthetic oligonucleotides mixture SEQ ID NO: 4. The reaction mix contained also 1 unit rTAQ polymerase (Pharmacia), 200 µM dNTP, 50 mM KCl, 1.5 mM MgCl$_2$ and 10 mM Tris-HCl pH 9.0 in a final volume of 25 µl. After 4 min of denaturation at 94° C., 25 cycles of [30 s 94° C., 30 s 50° C. and 45 s 72° C.] were performed followed by 7 min of elongation at 72° C. Only one fragment of 0.3 kb length was amplified as revealed by agarose gel electrophoresis.

1 µl of the PCR reaction described above was directly sequenced on a ABI 377 Sequencer (Applied Biosystems) with either 3 pmoles synthetic oligonucleotides mixtures SEQ ID NO: 2 or SEQ ID NO: 3 as primers. The sequencing with the oligonucleotides SEQ ID NO: 2 and SEQ ID NO: 3 gave the nucleotide sequences SEQ ID NO: 5 and SEQ ID NO: 6, respectively.

SEQ ID NO: 5:
CNAGTACAACAACGNNAAGNCCGGCNAATACAGNGTGNANTGGAAGAACT

GCGGNTATTTCACCTCTGGCAAGGGCTGGANNACTGGTAGNGCCCGGTAA

GT

SEQ ID NO: 6:
CGGCNAATACAAGGGTGTNANTGGAAGAACTGCGGNNATTTCACCTCNGG

CAAGGGCTGGACTACTGGTAGTGCCCGGTAAGTGCAA

A homology search with the above-mentioned sequences against the NCBI proteins database (5 Jan. 99) using the BLASTX 2.0.8 software found the best homology with the endo-β-1,4-xylanase A from *Chaetomium* (Accession number: dbj|BAA08649).

Southern Blotting of the *Penicillium griseofulvum* A160 Genomic DNA

Genomic DNA (0.5 µg) was digested overnight at 37° C. with either 2 units of the restriction enzyme EcoRI (Pharmacia), or 2 units each of restriction enzymes BamHI and EcoRI (Pharmacia), or 2 units of each restriction enzymes EcoRI and XbaI in a final volume of 20 µl (buffer: 1× One-Phor-All buffer PLUS (Pharmacia)). The digested DNAs were loaded on a 0.8% agarose gel in 1×TBE buffer. After electrophoresis, the restricted fragments were transferred onto a Hybond-N+ membrane (Amersham). The PCR fragments described above (1 µl) were labeled with digoxigenin using the DIG High Prime DNA Labeling and Detection Starter Kit II (Boehringer Mannheim). The membrane was hybridized overnight at 42° C. in the presence of a standard hybridization buffer (SSC 5×, formamide 50%, N-lauroylsarcosine 0.1%, SDS 0.02%, Blocking reagent) and a probe concentration of approximately 10 ng/ml (denatured for 5 min at 97° C.). After the hybridization, the membrane was first washed at 55° C. with 2×SSC, 0.1% SDS (2×15 min) followed by 3 washes with a 0.5×SSC, 0.1% SDS solution (30 min). After immunological detection, the hybridizing bands were identified by a four hour exposure to Kodak X-OMAT AR film at room temperature.

Figure 2:
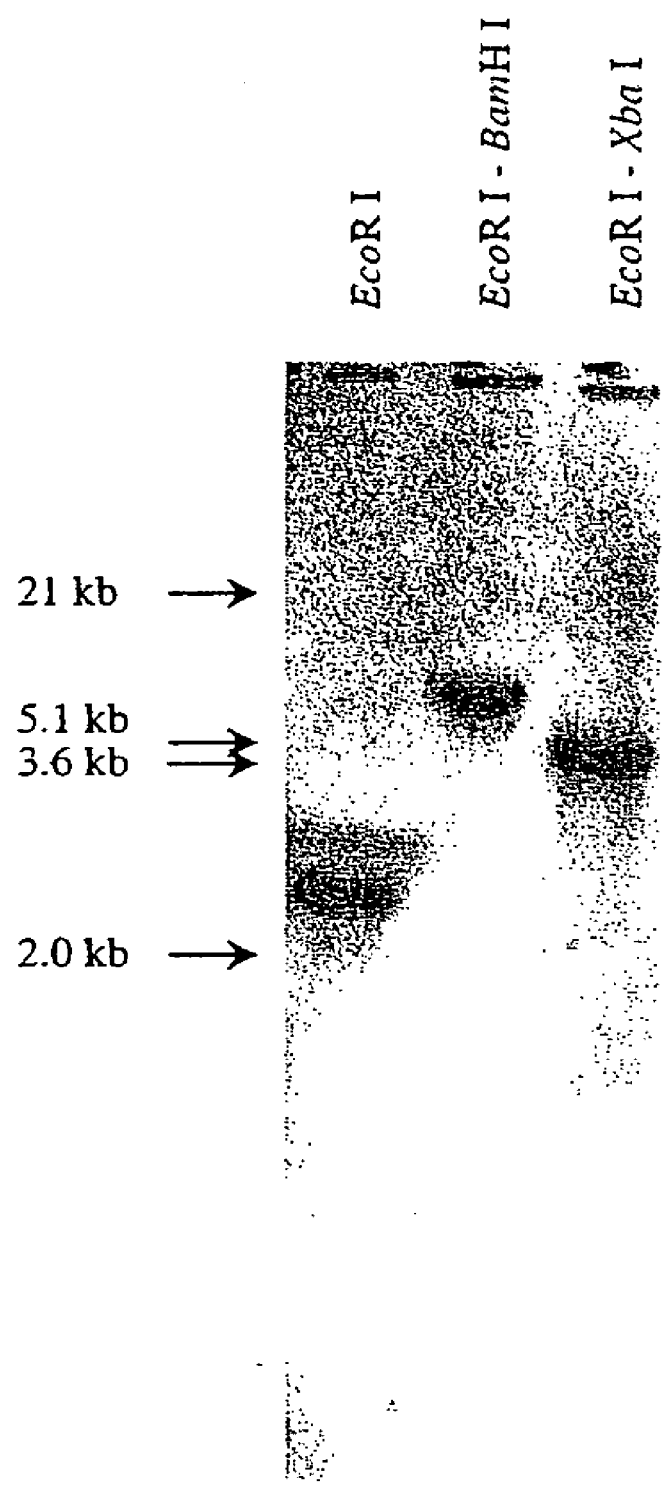
FIG. 2 shows a Southern blot analysis of the *Penicillium griseofulvum* A160 genomic DNA.

The results of the hybridization experiment are shown on the FIG. 2. It revealed that under the hybridization conditions tested, one DNA fragment hybridized with the probe.

Construction of a gDNA Restriction Fragments Library of *Penicillium griseofulvum* A160

Genomic DNA (5 µg) was digested overnight at 37° C. with 10 units each of restriction enzymes EcoRI and BamHI (Pharmacia) in a final volume of 100 µl. The restriction fragments were separated by electrophoresis on a 0.8% agarose gel, 1×TBE. A piece of the gel corresponding to fragments between 3.5 kb and 2.5 kb in length was removed and DNA was purified out of the agarose gel using the QIAQuick gene extraction kit (QIAGEN) in a final volume of 30 µl.

The purified fragments were inserted by ligation between the EcoRI and BamHI restriction sites of the pBluescript II SK(+) vector (Stratagene). 1 µg of pBluescript SK(+) plasmid DNA was first digested with 5 units each of EcoRI and I restriction enzymes (Pharmacia) in 50 µl (37° C., 16 h) and subsequently purified from both enzymes using the QIAQuick gene extraction kit. The ligation was performed using 3 µl of purified genomic DNA fragments, 0.25 µg of digested pBluescript SK(+) DNA, 3 units of T4 DNA ligase (Pharmacia), 1 mM ATP in a final volume of 30 µl (1× One-Phor-All buffer PLUS, 16° C., 16 h). the ligation mixture was then dialysed on a VSWP 013 membrane (Millipore) against water for 20 min. 1 µl of this mixture was electroporated into 40 µl electrocompetent *Escherichia coli* DH10b cells (BRL-Gibco) according to the manufacturer's protocol. After electroporation, cells were plated on LB plates supplemented with 100 µg/ml ampicillin to select for the transformed cells.

The above-described library was screened progressively using PCR reactions on pools of transformants of decreasing sizes. The PCR reaction conditions were the same as described above with the exception that the template DNA was the plasmids from the pooled *Escherichia coli* transformants purified from 3 ml cultures with the High Pure Plasmid Isolation Kit (Boehringer Mannheim). A 0.3 kb fragment was amplified in one clone out of approximately 1000 clones analyzed. The plasmid (pPGXYNA) recovered from this clone (LMBP-3987) contained one EcoRI-BamHI insert of 3 kb length. A partial sequence of the pPGXYNA plasmid comprising the xylanolytic enzyme coding sequence was determined on both strands by primer walking using among others the oligonucleotide with the sequence SEQ ID NO: 7 as primer.

```
SEQ ID NO: 7:
TAT TTC ACC TCT GGC AAG GGC T
```

The nucleotide sequence SEQ ID NO: 8 according to the invention codes for an amino acid sequence SEQ ID NO: 11 and the localization of an intron was deduced from alignments of the *Penicillium griseofulvum* A160 sequence with the most homologous xylanase protein sequences obtained from a homology search in GENBANK with the BLASTP 2.0.8 software (Altschul et al. 1997 *Nucl. Acids Res.* 25:3389). This localization was confirmed by the presence of the putative lariat-formation internal sequence and with the definition of the consensus 5' and 3' splice-junction sequences ('GT-AG' rule). The sequences SEQ ID NO: 9 and SEQ ID NO: 10 are the sequences encoding the two exons of the enzyme with xylanolytic activity. The sequence SEQ ID NO: 11 is the amino acid sequence of the *Penicillium griseofulvum* A160 enzyme. A signal sequence driving the secretion of the enzyme covers the first 27 amino acids of the sequence (FIG. 3).

A BLAST homology search was made with the *Penicillium griseofulvum* xylanase amino acid sequence SEQ ID NO: 11 of the invention. The BLAST tools that have been used are those available from the ncbi.nlm.nih.gov website. The closest homologue whatsoever that could be found, a *Penicillium* sp.40 xylanase A, has less than 80% sequence identity with SEQ ID NO: 11 (over the entire length).

EXAMPLE 4

Expression of the Xylanolytic Enzyme Gene in *Aspergillus oryzae*

Construction of Expression Vectors

A DNA fragment covering the coding region as well as its terminator region was amplified by PCR. The first synthetic oligonucleotide SEQ ID NO: 12 was chosen to contain the ATG codon corresponding to the first methionine of the coding region of the polypeptide gene as well as a recognition site for the restriction enzyme EcoRI. The second oligonucleotide SEQ ID NO: 13 corresponded to the sequence located 250 bp downstream of the last codon and contained a XbaI restriction site.

```
SEQ ID NO: 12:
GGAATTCCATAATGGTCTCTTTCT

SEQ ID NO: 13:
GCTCTAGAGCCACTTGTGACATGCT
```

Both primers (40 pmoles) were used for a PCR reaction with approximately 40 ng of pPGXYNA plasmid DNA as template. The 100 µl PCR reaction also contained 2.5 units Pfu DNA polymerase (Stratagene) and 1 µg BSA in the following buffer: Tris-HCl pH 8.0 20 mM, KCl 10 mM, $MgCl_2$ 2 mM, $(NH4)_2SO_4$ 6 mM and Triton X-100 0.1%. After denaturation of the DNA for 4 min at 94° C., 20 cycles of elongation were performed [30 s at 94° C., 30 s at 55° C. and 60 s at 72° C.] followed by an elongation step of 7 min at 72° C. The amplified DNA fragment was purified with the QIAQuick PCR purification kit (Qiagen) according to the manufacturer's protocol and recovered in a final volume of 50 µl. The extremities of the fragment were removed by digestion with the EcoRI and XbaI restriction enzymes (5 units of XbaI and 5 units of EcoRI enzymes (Pharmacia), 1× One-Phor-All buffer PLUS, final volume 60 µl, 37° C., overnight). The fragment was then purified with the QIAQuick gel extraction kit (Qiagen) after separation by electrophoresis on an agarose gel and recovered in 30 µl water.

The PCR DNA fragment was inserted between the EcoRI and XbaI restriction sites of the pBluescript II SK(+) vector (Stratagene). The vector was prepared as follows: 0.5 µg pBluescript SK(+) DNA was digested with 5 units EcoRI and 5 units XbaI restriction enzymes (Pharmacia) (final volume 20 µl, 2× One-Phor-All buffer PLUS, 37° C., overnight). After separation by electrophoresis in an agarose gel, it was purified with the QIAQuick gel extraction kit (Qiagen) and recovered in 30 µl water.

2 µl of PCR DNA fragment were ligated with this vector (1 µl) in the presence of ATP (1 mM), 1 unit of T4 DNA ligase (Pharmacia) and 1× One-Phor-All buffer PLUS (final volume 10 µl, 16° C., overnight). 1 µl of the ligation mixture was electroporated into electrocompetent *Escherichia coli* DH 10b cells (BRL-Gibco) after dialysis against water. A clone was selected after analysis of a number of transformants plasmids by extraction, digestion with appropriate restriction enzymes and separation by electrophoresis on an agarose gel using standard procedures. The new plasmid was termed pPGXYN1E-X.

The promoter of the glyceraldehyde-3-P dehydrogenase gene from *Aspergillus nidulans* was cloned in front of the xylanolytic enzyme gene. This promoter allows a strong constitutive transcription of the genes located downstream of it (Punt et al. 1990 *Gene* 93:101; Punt et al. 1991 *J Biotechnol.* 17:19). The plasmid pFGPDGLAT2 contains this promoter between two restriction sites: EcoRI and NcoI. This promoter was inserted into the pBluescript II SK(+) plasmid between two EcoRI restriction sites to give the pSK-GPDp plasmid using standard procedures. This plasmid (1 µg) as well as pPGXYN1E-X (1 µg) were digested by the EcoRI restriction enzyme (5 units) in the presence of 1× One-Phor-All buffer PLUS (final volume 10 µl, 37° C., overnight). The DNA fragments of interest were then separated by electrophoresis on an agarose gel and purified with the QIAQuick gel extraction Kit (Qiagen) and collected in 30 µl water. The purified promoter DNA fragment (1 µl) was inserted by ligation between the EcoRI recognition sites of pPGXYN1E-X (1 µl) in the presence of ATP (1 mM), 1 unit of T4 DNA ligase (Pharmacia) and 1× One-Phor-All buffer PLUS (final volume 10 µl, 16° C., overnight). 1 µl of the ligation mixture was electroporated into electrocompetent *Escherichia coli* DH10b cells (BRL-Gibco) after dialysis against water. A clone was selected after analysis of a number of transformant plasmids by extraction, digestion with appropriate restriction enzymes and separation by electrophoresis on an agarose gel using standard procedures. The new plasmid was termed PGPDp-PGXYN1.

Transformation of *Aspergillus oryzae*

The strain *Aspergillus oryzae* MUCL 14492 was transformed by generating protoplasts according to the protocol described by Punt et al. (1992 *Meth. Enzymol.* 216:447). The pGPDp-PGXYN1 plasmid was cotransformed with the p3SR2 plasmid that contains a selection marker used to recover transformants (the *Aspergillus nidulans* acetamidase gene—Hynes et al. 1983 *Mol. Cell. Biol.* 3:1430). Transformants were selected on minimum medium plates containing acetamide as sole nitrogen source.

The strain *Aspergillus oryzae* MUCL 14492 was grown in 500 ml *Aspergillus* Minimum Liquid medium (Pontecorvo et al. (1992)) for 16 hours at 30° C. The culture was filtered through a Miracloth filter to collect the mycelium. The mycelium was washed with the Osm solution (CaCl$_2$ 0.27 M, NaCl 0.6 M) and then incubated with 20 ml solution Osm/g mycelium supplemented with 20 mg Novozym 234 (Sigma). After 1 hour at 30° C. with slow agitation (80 rpm), the protoplasts were formed and the suspension was placed on ice. The protoplasts were separated from intact mycelium by filtration through a sterile Miracloth filter and diluted with 1 volume STC1700 solution (sorbitol 1.2 M, Tris-HCl pH 7.5 10 mM, CaCl$_2$ 50 mM, NaCl 35 mM). The protoplasts were then collected by centrifugation at 2000 rpm for 10 min at 4° C. and washed twice with STC1700 solution. They were resuspended in 100 µl of STC1700 (10$^8$ protoplasts/ml) in the presence of 3 µg p3SR2 plasmid DNA and 9 µg pGPDp-PGXYN1 plasmid DNA. After 20 min at 20° C., 250 µl, 250 µl and 850 µl PEG solution (PEG 4000 60%, Tris-HCl pH 7.5 10 mM and CaCl$_2$ 50 mM) were added successively and the suspension was further incubated for 20 min at 20° C. PEG treated protoplast suspensions were diluted by the addition of 10 ml STC1700 and centrifugated at 2000 rpm for 10 min at 4° C. The protoplasts were then resuspended in 200 µl STC1700 and plated onto *Aspergillus* Minimum Agar Medium and osmotically stabilized with 1.2 M sorbitol. To select the transformants, the nitrogen sources in the plates were replaced by 10 mM acetamide and 12 mM CsCl.

Analysis of *Aspergillus oryzae* Transformants 48 transformants were analyzed for the xylanolytic enzyme expression. They were grown in *Aspergillus* Minimum Liquid Medium supplemented with 3% sucrose as carbon source and 0.5% Bacto yeast extract (Difco). After 75 hours at 30° C. and 130 rpm, the supernatant of the cultures was assayed for xylanolytic activity. Ten of the transformants showed a significantly higher xylanolytic activity as compared to a control strain transformed only with the p3SR2 plasmid.

EXAMPLE 5

Characterization of the Enzyme with Xylanolytic Activity from *Penicillium griseofulvum* A160

Purification of the Enzyme with Xylanolytic Activity Expressed in *Aspergillus oryzae*

The enzyme with xylanolytic activity expressed in *Aspergillus oryzae* was purified in order to separate it from the traces of alpha-amylase present in the culture supernatants of the transformants. 10 ml of a culture supernatant from a selected transformant were diluted 3 times to reach a final concentration of 50 mM in sodium acetate pH4.2.

This solution was located at 2 ml/min on a Pharmacia XK16/20 column filled with approximately 30 ml of the Bio-Rad Macro High S resin equilibrated in 50 mM sodium acetate pH 4.2. Proteins were eluted with a linear increasing NaCl gradient from 0 M to 0.6 M in 50 mM sodium acetate pH 4.2. Xylanase and amylase activities were determined in the eluted fractions. The amylase activity was recovered in the flow through fractions while the xylanase activity was eluted approximately at 0.1 M NaCl. The active fractions with xylanolytic activity were pooled and kept for further analysis.

Optimum pH and Temperature

Figure 4:
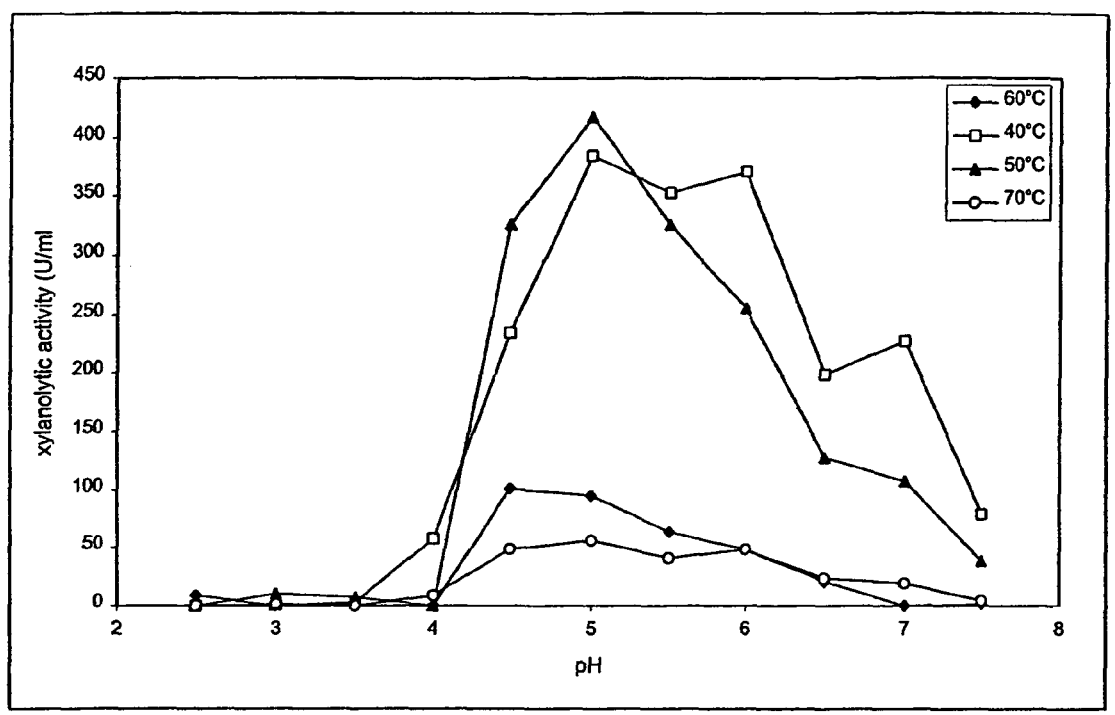
FIG. 4 shows the effect of the temperature and of the pH on the xylanase activity.

The pH and temperature dependence of the activity of the xylanolytic enzyme secreted by one *Aspergillus oryzae* transformant was analyzed. The activity was measured in a citrate/phosphate buffer (0.1 M) at various pH (FIG. 4). The maximum activity was observed around 50° C. At this temperature, the optimum pH was about 5.0. These properties are similar to those of the enzyme with xylanolytic activity purified from the *Penicillium griseofulvum* A160.

EXAMPLE 6

Baking Trials

Baking trials were performed to demonstrate the positive effect of the *Aspergillus griseofulvum* A160 xylanase in baking. The positive effect was evaluated by the increase in bread volume compared to a reference not containing the enzyme.

The xylanase was tested in Belgian hard rolls that are produced on a large scale every day in Belgium. The procedure described is well known to the craft baker and it is obvious to one skilled in the art that the same results may be obtained by using equipment from other suppliers.

The ingredients used are listed in Table 1 below:

TABLE 1

| Ingredients (g) | RECIPE 1 | RECIPE 2 | RECIPE 3 | RECIPE 4 | RECIPE 5 |
|---|---|---|---|---|---|
| Flour (Surbi -- Molens van Deinze) | 1500 | 1500 | 1500 | 1500 | 1500 |
| Water | 915 | 915 | 915 | 915 | 915 |
| Fresh yeast (Bruggeman -- Belgium) | 90 | 90 | 90 | 90 | 90 |
| Sodium chloride | 30 | 30 | 30 | 30 | 30 |
| Ascorbic acid | 0.12 | 0.12 | 0.12 | 0.12 | 0.12 |
| Multec Data 2720S ™ | 3.5 | 3.5 | 3.5 | 3.5 | 3.5 |
| Dextrose | 10 | 10 | 10 | 10 | 10 |
| Xylanase ™ A160 (Megazyme units) | 0 | 23 | 35 | 52 | 70 |

The ingredients were mixed for 2 min at low speed and 7 min at high speed in a Diosna SP24 mixer. The final dough temperature as well as the resting and proofing temperatures were 25° C. After resting for 15 min at 25° C., the dough was reworked manually and rested for another 10 min. Afterwards, 2 kg dough pieces were made up and proofed for 10 min. The 2 kg dough pieces were divided and made up using the Eberhardt Optimat. 66 gr round dough pieces were obtained. After another 5 min of resting time, the dough pieces were cut by pressing and submitted to a final proofing stage for 70 min.

The dough pieces were baked at 230° C. in a Miwe Condo™ oven with steam (Michael Wenz—Arnstein—Germany). The volume of 6 rolls was measured using the commonly used rapeseed displacement method.

The results are presented in Table 2 below:

TABLE 2

| Xylanase units | Volume (ml) |
|---|---|
| 0 | 2125 |
| 23 | 2475 |
| 35 | 2550 |
| 52 | 2675 |
| 70 | 2775 |

Figure 5:
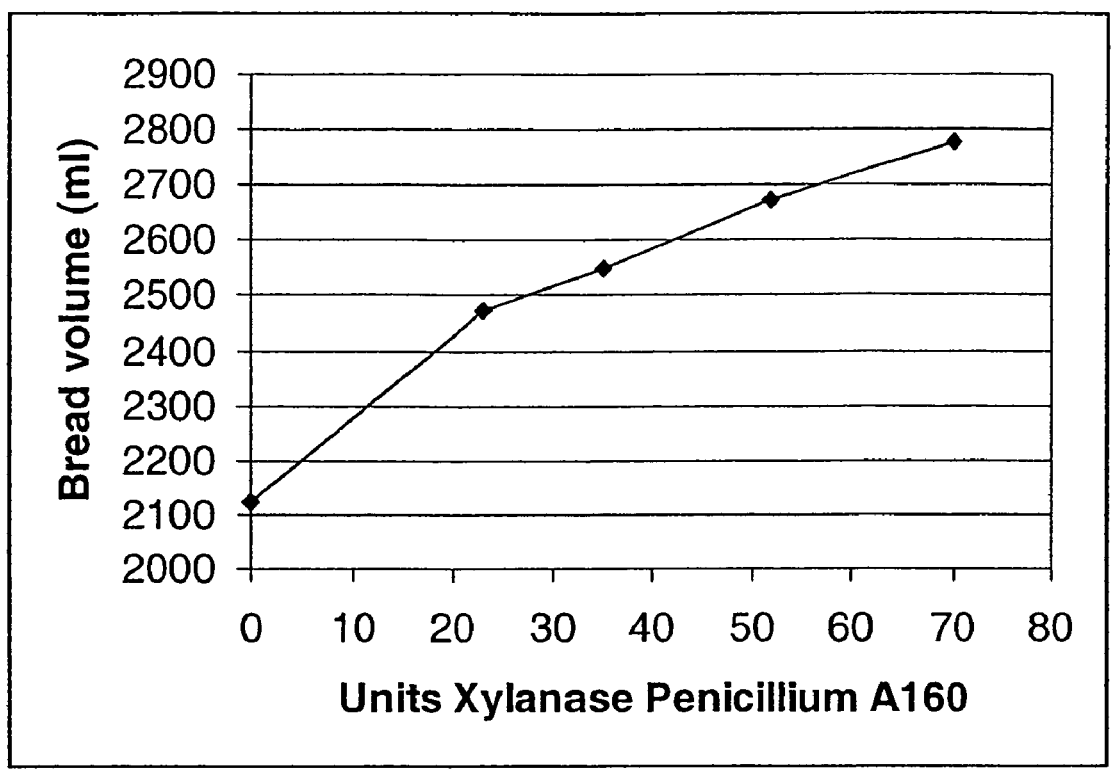
FIG. 5 represents the increase of a bread volume according to the enzymatic activity of the xylanase according to the invention.
Figure 7:
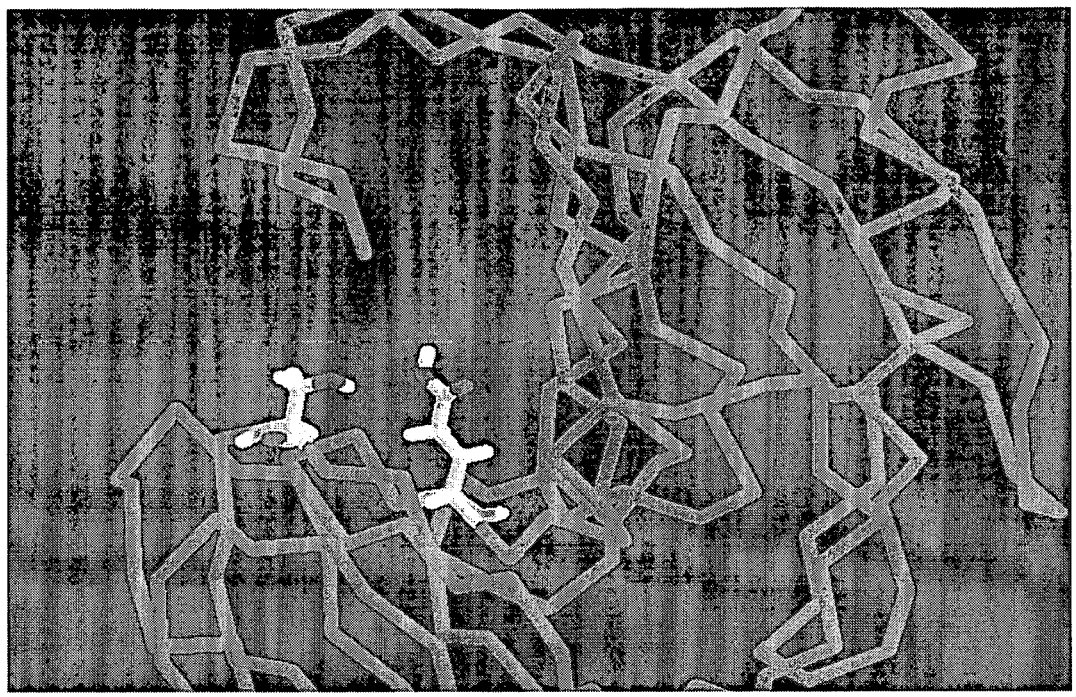
FIG. 7 shows the Ser44 and Glu177 of the *P. griseofulvum* family 11 (formerly G) xylanase. Main chain (grey), Ser44 (left, white), Glu177 (right, white).

A graphical representation of the effect of the xylanase on bread volume is shown in FIG. 5.

EXAMPLE 7

Effect of the Enzyme on the Flour Viscosity in the Presence of Water

Purified xylanase was used for the test. The enzyme was purified as described in Example 5.100 g of wheat flour (Surbi, Molens van Deinze) were mixed manually with 117 ml water containing 25 xylanase units of the enzyme with xylanolytic activity from *Penicillium griseofulvum* A160. After 15 min at 36° C., the viscosity was measured (Programmable DV-II+ Viscometer, Helipath system, Spindel F, Brookfield). The speed was maintained at 4 rpm and the viscosity value was measured after 10 s. The viscosity of a blank sample was obtained in the same way with untreated flour. The same experiment was also carried out with 10 units of the best performing enzyme available actually on the market (*Aspergillus aculeatus* xylanase available from Novo Nordisk (Shearzyme™ L)). Each experiment was performed in triplicate. The viscosity results presented in Table 3 below are expressed in centipoises.

TABLE 3

| Blank sample | 116.000 +/− 2000 |
|---|---|
| *Penicillium griseofulvum* enzyme | 65.034 +/− 5047 |
| *Aspergillus aculeatus* xylanase | 68.959 +/− 2253 |

*Aspergillus aculeatus* xylanase was shown to give better results than xylanases from *Humicola insolens, Trichoderma reesei* (Spezyme CP, Genencor) and another xylanase from *Aspergillus aculeatus* (xylanase I) (Patent application WO 94/21785). Christophersen et al. (Christophersen et al. 1997 Starch/Starke 49:5) also showed the better performance of *Aspergillus aculeatus* xylanase as compared to a xylanase from *Thermomyces lanuginosus* and two commercial hemicellulase cocktails sold for wheat separation.

The results presented above showed that the enzyme with xylanolytic activity from *Penicillium griseofulvum* A160 has the biggest capacity of reducing the viscosity of flour suspended in water.

EXAMPLE 8

Wheat Separation

When mixed with water, the flour may be separated into a starch, a gluten, a sludge and a soluble fraction by centrifugation. A decrease of the sludge fraction leads to a better wheat separation. The performances of a pure xylanase can therefore be evaluated by measuring the decrease of the solid sludge fraction after centrifugation.

Such experiment has been carried out with the purified enzyme with xylanolytic activity from *Penicillium griseofulvum* A160 of Example 5 compared to Sherzyme™ L.

100 g of wheat flour (Surbi, Molens of Deinze) were mixed manually with 117 ml water containing different concentrations of enzyme. After 15 min at 35° C., the mixture was centrifugated for 10 min at 4000 g (Varifuge 3.0R, Heraeus Sepatech). The liquid phase was weighed.

Table 4 below shows the results of a typical experiment, by reporting the relative increase of the liquid phase induced by the presence of the xylanolytic enzyme. The enzyme from *Penicillium griseofulvum* A160 allowed to reach a higher liberation of liquid than Shearzyme™ L.

TABLE 4

| Enzyme (units/test) | *P. griseofulvum* enzyme (%) | Shearzyme ™ L (%) |
|---|---|---|
| 0 | 100 | 100 |
| 3.125 | 110 | 127 |
| 6.25 | 129 | 130 |
| 12.5 | 134 | 134 |
| 25 | 166 | 137 |

EXAMPLE 9

Functional Homologues of SEQ ID NO: 11

Many substitutions can be made in the family 11 (formerly G) xylanases sequences without losing enzymatic activity. This will be demonstrated below.

FIG. 6 shows the alignment of ten representative xylanase sequences that were publicly available in 2000. A similar alignment can be made with all the sequences actually stored as family 11 (formerly G) members (see for instance the afmb.cnrs-mrs.fr/CAZY web site, section Glycosidases and Transglycosidases, family 11). Seventy four family 11 xylanase sequences were known at the time the present application was filed. The number of sequences stored as family 11 (formerly G) members has more than doubled since 2000.

From the examination of such alignments (see for instance FIG. 6) one can see that that very few amino acids are totally conserved among all sequences. Others are conserved in some of the sequences only. The differences in amino acids at some positions are in part due to conservative substitutions.

From such alignments, those skilled in the art can derive where in the amino acid sequence of a family 11 (formerly G) xylanase, amino acid substitutions are tolerated and do not affect the enzymatic activity of a xylanase.

The alignment data provide a first yet important indication of where in the amino acid sequence of SEQ ID NO: 11 modifications (e.g. replacements or substitutions) are tolerated and where not. At some places/sites in the amino acid sequence of SEQ ID NO: 11 modifications (e.g. replacements or substitutions) will not be tolerated or will not be tolerated without affecting the (xylanase) activity of the enzyme. Highly conserved residues, e.g., are preferably maintained, especially those completely conserved and involved in the catalytic activity like the two essential glutamic acid residues, which act as a nucleophile and acid/base catalyst, respectively in the double displacement reaction mechanism of the xylanase. More information on which residues are preferably maintained in SEQ ID NO: 11 is given in the description and the Examples provided in sequel.

At other places/sites in the amino acid sequence of SEQ ID NO: 11 modifications (e.g. replacements or substitutions) will be tolerated. Depending on the situation, it may be possible to replace an amino acid by another one having the same type of side chain (e.g., threonine vs serine), or by an amino acid having a different kind of side chain (e.g., alanine vs serine) (Argos et al. 1979 *Biochemistry* 18-25:5698-5703).

It is meant by a "conservative amino acid substitution" the replacement of an amino acid with another amino acid having a comparable side chain (i.e. a side chain with the same properties, e.g. Leu vs Ile). By such replacement the enzymatic activity is not affected, at least not significantly affected. Such groups of amino acids are known in the art and include amino acids with basic side chains (e.g., lysine, arginine and histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (threonine, valine, isoleucine) and aromatic side chains (e.g., tyrosine, phenylalanine, tryptophan, histidine) (see, for instance, Molecular Cell Biology, Darnell et al. (eds), 1986 *Scientific American Books*, p. 54).

It is meant by a "neutral amino acid substitution" an amino acid replacement that does not affect or does not significantly affect [due to the limit of measurements of evaluation techniques] the functionality and activity of an enzyme, for instance a polypeptide with xylanolytic activity like SEQ ID NO: 11.

Active Sites or Important Domains of Family 11 (Formerly G) Xylanases are Known

Information derivable from sequence alignments preferably is complemented with published information on active sites or important domains of the enzyme in question. Ample information is available on active sites and important domains of family 11 (formerly G) xylanases. For example, Kulkarni et al. 1999 *FEMS Microbiology Reviews* 23:411-456, incorporated by reference herein), describes amino acids involved in catalysis (p. 429-431 chapters 9 and 10.1) and the modification of the xylanase sequence in order to modify its enzymatic properties while still keeping the xylanase activity (p. 431 chapter 10.2). More information is provided in Wakarchuk W. W. et al. 1994 *Protein Science* 3:467-475; Ko E. P. 1992 *Biochem J.* 288:117-121; Törrönen A. 1995 *Biochemistry* 34:847-856), incorporated by reference herein. This information on active sites and important domains holds for all xylanases in this family and those skilled in the art know how to translate this information to the xylanase of the invention, SEQ ID NO: 11.

Creation and Testing of Mutant Forms of SEQ ID NO: 11

Mutants of xylanases have been described. See, for example, the articles mentioned above and Arase A. et al. 1993 *FEBS Letters* 316:123-127, incorporated by reference herein.

Techniques known in the art can be used to create mutant forms or variants of SEQ ID NO: 11. For instance variant and mutant forms of SEQ ID NO: 11 may be created via site-directed mutagenesis. Once a DNA sequence encoding an enzyme with xylanolytic activity, e.g. SEQ ID NO: 8, has been isolated, and desirable sites for mutation (modification) have been identified, mutations (modifications) may be introduced using synthetic oligonucleotides. These oligonucleotides contain nucleotide sequences flanking the desired mutation sites; mutant nucleotides are inserted during oligonucleotide synthesis. In a specific method, a single stranded gap of DNA, bridging the xylanase-encoding sequence, is created in a vector carrying the xylanase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into xylanase-encoding DNA sequences is described in Nelson and Long (1989 *Anal Biochem.* 180:147-151), incorporated by reference herein. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction-endonucleases and reinserted into an expression plasmid.

Alternative methods for providing variants of the invention include gene shuffling, e.g., as described in WO95/22625 (from Affymax Technologies N. V.) or in WO 96/00343 (from Novo Nordisk A/S), or other corresponding techniques resulting in a hybrid enzyme comprising the mutation (s), e.g., substitution (s) and/or deletion (s), in question.

A DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes. In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell. The same or similar cloning strategies as described for SEQ ID NO: 11 may be used for the mutant or variant forms of SEQ ID NO: 11 here described.

Those skilled in the art knew in 2000 how to create and test large collections of enzyme variants or mutants of SEQ ID NO: 11. Methods for generating large collections of enzyme variants, e.g., existed at the time of filing. Information on how to generate large numbers of mutated forms of a particular gene can be found, for example, in the following references and in particular in the Materials and Methods sections thereof: Stemmer W. 1994 *PNAS USA* 91:10747-10751; and Giver L. et al. 1998 *PNAS USA* 95:12809-12813, incorporated by reference herein. Commercial kits are also available to scientists to rapidly obtain mutants or variants (example: GeneMorph® II EZClone Random Mutagenesis Kit from Stratagene).

Many assays exist in the art for measuring xylanase activity of a (variant) enzyme, whereby the activity of the variant enzyme can be easily compared with that of the enzyme of SEQ ID NO:11 (or any other enzyme with xylanolytic activity). An example of a test to measure xylanase activity is provided in Example 1, under "Determination of the xylanolytic activity".

In addition to that, methods for high-throughput screening of enzyme (xylanase) variants existed in 2000. Many publications describe methods to perform high-throughput screening of large collections of enzyme mutants or variants. See for example: Olsen, M., et al. 2000 Curr. Opin. Biotechnol 11:331-337; and Olsen, M., et al. 2000 Nature Biotechnology 18:1071-76, incorporated by reference herein. Several private companies also offer services to perform high-throughput screening, sometimes combined with mutant library construction (Kairos, Protéus, Diversa, etc.). These techniques may be used to test variants and mutant forms of SEQ ID NO: 11.

In conclusion, those skilled in the art would have been able to identify, positions at which amino acid substitutions are tolerated without risking the loss of xylanolytic activity. In 2000 already there were sufficient sequences to compare, and literature existed on important active sites and important domains of family 11 (formerly G) xylanases, the family to which the xylanase with SEQ ID NO: 11 belongs. In addition to that, several publications on mutant xylanases existed. Methods for generating large collections of enzyme variants existed, and methods for high-throughput screening of (xylanase) enzymes already existed.

In sequel it will be shown how all this information available in the art can be used/implemented to generate variants of SEQ ID NO: 11 that preferably retain xylanolytic activity (or at least 80% of the xylanolytic activity of SEQ ID NO: 11).

Below a few examples are given of xylanase sequences that are at least 70, more preferably at least 80, 85 or 90% homologous (identical) to SEQ ID NO: 11. In silico techniques are used to demonstrate that mutant forms of SEQ ID NO: 11 with up to about 20% (e.g., up to about 5, 10, 12, 13, 14, 15, 16, 17, 18, 19, 20%) of the amino acids of SEQ ID NO: 11 being substituted or replaced are tolerated by the enzyme, which completely retains its structure and thereby also its functionality and function.

Family 11 xylanases in se appear to be more permissive to drastic mutations without modification of their behavior (activity and stability versus pH and temperature, specific activity). In silico mutations made to improve enzyme properties gave several enzymes unchanged. A potential engineered salt bridge designed in Xyl1 of *Streptomyces* sp S38 (A82R and Y170D), e.g., resulted in a mutant with the same properties as the wild-type enzyme (Georis et al 2000 *Protein Sci.* 9:466-475). Multiple combinations of engineered arginines in sites on the protein surface of XynII of *T. reesei* (K58R and A160R; K58R, A160R and N97R; K58R, A160R, N97R and N67R; K58R, A160R, N97R, N67R and T26R) did not increase the thermostability of the mutant enzymes, which had a quite similar pH-dependent activity profile (Turunen et al. 2002 *Protein Eng.* 15-2:141-145). Several charged residues introduced in Xyl1 of *Streptomyces* sp S38 (S18E and Y186E; G50R and Y186E) left the mutated enzymes unchanged compared to the wild-type (De Lemos Esteves et al. 2004 *Protein Sci.* 14:292-302). All above-cited references are incorporated by reference herein.

Also SEQ ID NO: 11 appears to be permissive to modifications, even rather drastic modifications, without change in its behavior. The sequences given below are examples of mutant and variant forms of SEQ ID NO: 11 that the skilled person was able to create and test, in 2000 already, without any undue burden.

EXAMPLE 10

A Sequence about 90% Homologous (Identical) to SEQ ID NO: 11

Construction of a Molecular Model of the Wild-Type Enzyme of the Invention

A first 3D model of the *P. griseofulvum* family 11 xylanase has been built by using the *Penicillium funiculosum* family 11 xylanase (Payan et al. 2004 *J Biol Chem.* vol. 279: 36029-37, incorporated by reference herein) coordinates as template. Indeed, SEQ ID NO: 11 is about 64% identical to this xylanase: 121 out of 189 amino acid being identical and only 1 gap. It was the best candidate found. The molecular model could, however, have been equally well built based on 3D-structures published in 1994.

The selected candidate has been running with Modeler6v2 to build the 3D-model as published by Sali et al (1993 *J. Mol. Biol.* 234:779-815 incorporated by reference herein) and then a Procheck program to check the allowed Ramachandran zones. The target protein being refined at 2.5 Å, the built model has the same resolution.

Initially 10 models were generated and analyzed. Models numbered 3 and 5 were the best ones, all the amino acids being in the authorized Ramachandran zones, while other models had one or two residues out of these defined zones. The superimposition of the models 3 and 5 with the 3D structure 1TE1 of *Penicillium funiculosum* family 11 xylanase by using RasMol version 2.6, revealed their perfect superimposition. Both models 3 and 5 were submitted to energy minimization of their lateral side chains until the maximum derivative was less than 0.001 kcal/A, the main chain scaffold being conserved unminimized. After 2000 iterations, both models were energetically extremely close (−1004.3 kcal vs −1013.7 kcal). It was not possible to discriminate them on the basis of their energy discrepancy.

Analysis of this Molecular Model of the Wild-Type Enzyme

Amino acid sequences from family 11 xylanases (GH11) were retrieved from protein databases by blast and from phylogenetic studies published by Georis et al, (1999 *Gene* 237: 123-33, incorporated by reference herein) and aligned. Highly and poorly conserved regions were analyzed and secondary structures were examined (mainly beta-sheet structures).

Interestingly, this alignment revealed that *P. griseofulvum* family 11 xylanase presents an unusual Ser residue in position 44 of the mature enzyme while all "acidic" GH11 xylanases present an Asp residue and "alkaline" GH11 xylanases present an Asn residue at the corresponding position according to the sub-classification of GH11 proposed by Torrönen, A & Rouvinen, J. (1997 *J. Biotechnol.* 57:137-49, incorporated by reference herein). This Ser residue is well-known to establish hydrogen bonding with the acid/base catalytic residue Glu, thus leading to a change in the pKa value and in the optimum pH activity, as shown by Torrönen & Rouvinen (1995 *Biochemistry* 34:847-56, incorporated by reference herein). This Ser residue confers to the *P. griseofulvum* family 11 xylanase a unique natural feature compared to the other wild-type GH11 enzymes and should present a non-conventional influence on the pKa of the catalytic residue. FIG. 7 shows the Ser44 and Glu 177 of the family 11 (formerly G) xylanase of the invention.

It is highly preferred that the Ser residue at position 44, which appears to provide a unique characteristic to the xylanase of the invention, is not touched. Mutant or variant forms of SEQ ID NO: 11 preferentially have a Ser residue at position 44 or at any corresponding position.

Construction of a *P. griseofulvum* GH11 Model with about 10% Mutations

A scan with Prosite viewer of the amino acid of the *P. griseofulvum* family 11 xylanase allowed to identify different unusual signatures additional to the common features of the family 11 xylanase. Those motifs are: three putative CK2-Phospho sites (residues 3-6, 112-115, 132-135), nine putative myristyl N-myristoylation sites, a putative N-glycosilation site (res. 60-63) and a putative CAMP-Phospho site (144-147). Amino acid positions referred to are those in the mature enzyme.

The catalytic and related residues, the putative N-glycosilation sites, putative Phospho sites and the putative N-myristyl sites of the putative N-term part were maintained unchanged. Taking into account that the N-terminal part of the GH11s is crucial to their thermostability and thermophilicity (U.S. Pat. No. 5,759,840; Georis et al. 2000 *Protein Sci.* 9:466-75; Shibuya et al. 2000 *Biochem J.* 349:651-6; Fenel et al. 2004 *J Biotechnol.* 108:137-43 and Sun et al. 2005 *Protein Expr. Purif.* 42:122-30, all incorporated by reference herein), residues 1-30 from the mature enzyme in this example were kept unchanged.

Based on a blast performed on family 11 xylanases in a PDB database, the 3D structures of 1TE1, 1XY0 (Törrönen et al 1994 *EMBO J.* 13:2493-501; Törrönen & Rouvinen 1995 *Biochemistry* 34:847-56, incorporated by reference herein) and or 1HIX (Wouters et al. 2001 *Acta Crystallogr. D. Biol. Crystallogr.* 57:1813-9, incorporated by reference herein) were additionally selected and aligned to define positions where changes are tolerated. The selected positions are listed in Table 5. Positions and mutations selected to build the molecular model of *P. griseofulvum* family 11 xylanase are listed in bold in said Table 5. In A160: Amino acid residue as found in the WT A160 enzyme with xylanolytic activity from *Penicillium griseofulvum*; In 1XYO: Amino acid residue as found in the Törrönen et al, 1994, sequence; other possibilities: other possible amino acids found at a given position, according to BLAST alignment information. Amino acid positions referred to are those in the mature enzyme.

TABLE 5

| In A160 | In 1XY0 | Other possibilities | comments |
|---|---|---|---|
| A32 | G | N | |
| K40 | S | T, V, Q, E, A, R | End of sheet, not conserved |
| N41 | — | D | Low security, highly conserved |
| S44 | N | | Begin of sheet, active site vicinity |
| A52 | Q | N, S | |
| T53 | P | N | |
| S55 | K | N, A, G | |
| A56 | N | R, T, S | |
| R57 | K | Q, H, R | |
| N58 | V | D, T, A | |
| E94 | T | D, S | |
| S100 | G | | |
| M101 | A | L, G | |
| F103 | K | Y | |
| K104 | L | R, M | |
| T106 | E | Q, S | |
| V113 | — | T | |
| S131 | T | | |
| S132 | A | K, R | |

TABLE 5-continued

| In A160 | In 1XY0 | Other possibilities | comments |
|---|---|---|---|
| I140 | V | | |
| R142 | — | T, Q | |
| N143 | — | S, E, Q | Low security: K144 and R145 highly conserved |
| K144 | H | | Highly conserved |
| S146 | | T, V | |
| S147 | G | | |
| L162 | Q | Y, A, H | |
| M164 | L | | |
| S168 | T | N | |
| Q180 | F | K, E | |

In FIG. 8 the mutated sequence containing about 10% of mutations (referred to as M1P, SEQ ID NO: 15) is aligned with the wild-type sequence (WT or SEQ ID NO: 11).

The 3D-structure of 1XY0 has been selected as the most interesting one to represent the selected mutations. Indeed, the *P. griseofulvum* xylanase has 63% sequence identity with 1XY0 and presents in its wild type sequence lots of the mutations listed in bold characters in Table 5. The sequence identity as given in this paragraph is the % identity over the length of the mature enzyme.

A new molecular model of the *P. griseofulvum* family 11 xylanase was built based on the M1P sequence having SEQ ID NO: 15. It was performed with the same strategy as described for the model of the wild type. Based of this list of mutations, 10 models were generated.

Modeler and Procheck analysis revealed that all of them are of good quality. None of the side chain residues were out of the Ramachandran Plot.

Model one (1) was arbitrarily chosen for minimization, giving energetic values rather higher than those obtained with the model of the native sequence (−861.4 kcal), but this phenomenon seems to be normal. Moreover, the RMS (route mean square) corresponds to that of the side chains and should be lowered after thousands of iterations. No strong steric clashes were observed despite the rather high level of mutations.

A Blast retrieval made with the sequence about 89% homologous to SEQ ID NO: 11 has revealed 75% sequence identity with Xyn1 *T. reesei* (Torronen A et al. 1992 *Biotechnology* (N.Y.) 10:1461-1465). By way of comparison, the family 11 xylanase found to be closest to SEQ ID NO: 11—the xylanase from *Penicillium* sp.40 (Kimura et al. 2000 *Biosci. Biotechnol. Biochem.* 64:1230-1237)—has 77% sequence identity with SEQ ID NO: 11. The sequence identities given in this paragraph are the % sequence identity over the length of the mature enzyme.

EXAMPLE 11

A Sequence about 85.3% Homologous (Identical) to SEQ ID NO 11

Construction of a Model with about 14.7% Mutations

Multiple sequence alignments of all the family 11 xylanases available and a careful analysis of secondary structure elements, mainly beta-sheets, revealed other modifications potentially interesting, despite location around the catalytic loop, or despite being very close to beta sheets or highly conserved. These residues are T102, V107, T108, S109, S112, S129, R145, and L166. Amino acid positions referred to are those in the mature enzyme.

Table 6 summarizes the mutations allowed for these residues (located in the N-terminal part or C-terminal part of beta-sheets). Positions and the mutations selected (in the mature enzyme) to build the molecular model with 14.7% of mutations of the *P. griseofulvum* family 11 xylanase are shown in bold and underlined (column 2). In the first column the amino acid residues as found in the WT A160 enzyme with xylanolytic activity from *Penicillium griseofulvum* are given. The third column gives other possibilities at the given positions. Amino acid positions referred to are those in the mature enzyme.

Figure 10:
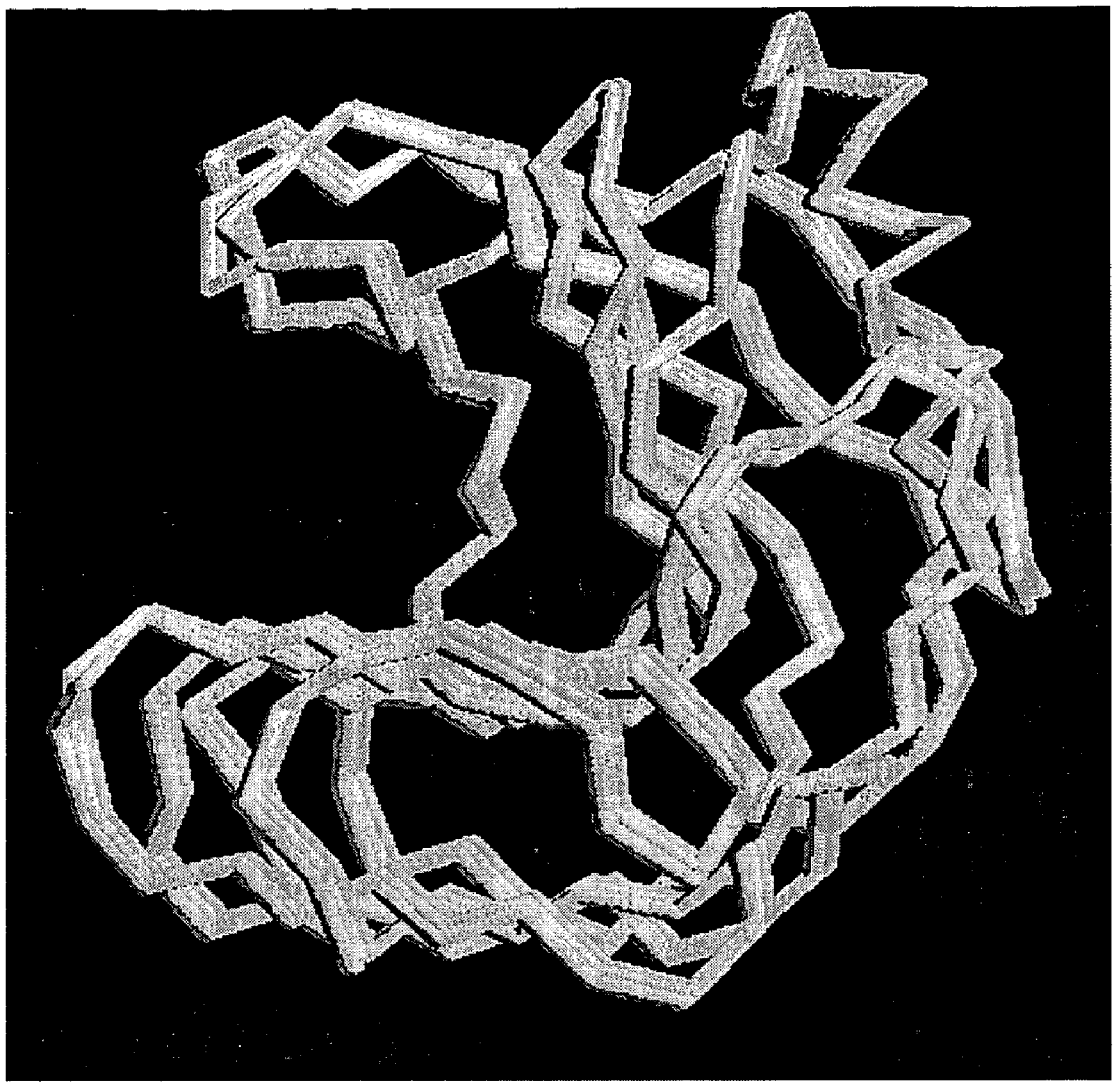
FIG. 10 represents a superimposition of the wild type enzyme model (WT), Model 10% (M1P) and the Model 14.7% (M2P).

Mutations were made in silico, starting from the Model with about 10% mutations (Model 10%), to give the Model with about 16% mutations (Model 16%). Side chains positions were optimized through energy minimization. Not surprisingly, the energetic value (−695.5 kcal) is higher than that obtained with the wild type model and the Model 10%. Once again, no volumic clashes were observed despite the high % of mutations. FIG. 10 represents a superimposition of both models and the 3D-structure of 1XYO, showing a perfect fit.

A Blast retrieval with the sequence about 85.3% homologous (identical) to SEQ ID NO: 11 has revealed 71% of identity with Xyn1 of *T. reesei* (Torronen, A et al. 1992 *Biotechnology* (N.Y.) 10: 1461-1465). By way of comparison, the family 11 xylanase found to be closest to SEQ ID NO: 11—the xylanase from *Penicillium* sp.40 (Kimura et al. 2000 *Biosci. Biotechnol. Biochem.* 64:1230-1237)—has 77% sequence identity with SEQ ID NO: 11. The sequence about 85.3% identical to SEQ ID NO: 11 is referred to as the M2P sequence having SEQ ID NO: 16. The sequence identities given in this paragraph are the % sequence identity over the length of the mature enzyme. The model that was built as such is referred to as the Model 14.7%.

TABLE 6

| In A160 | selected | Other possibilities | comments |
|---|---|---|---|
| T102 | S | Q, E | |
| V107 | L | F | Hydroph. Interaction with A158 |
| T108 | T | Q, E, N | Y or K less accepted |
| S109 | T | | Q not possible |
| S112 | A | G | |
| S129 | G | | |
| R145 | R | V | Interaction E90 |
| | | | Highly conserved |
| L166 | M | | |

Figure 9:
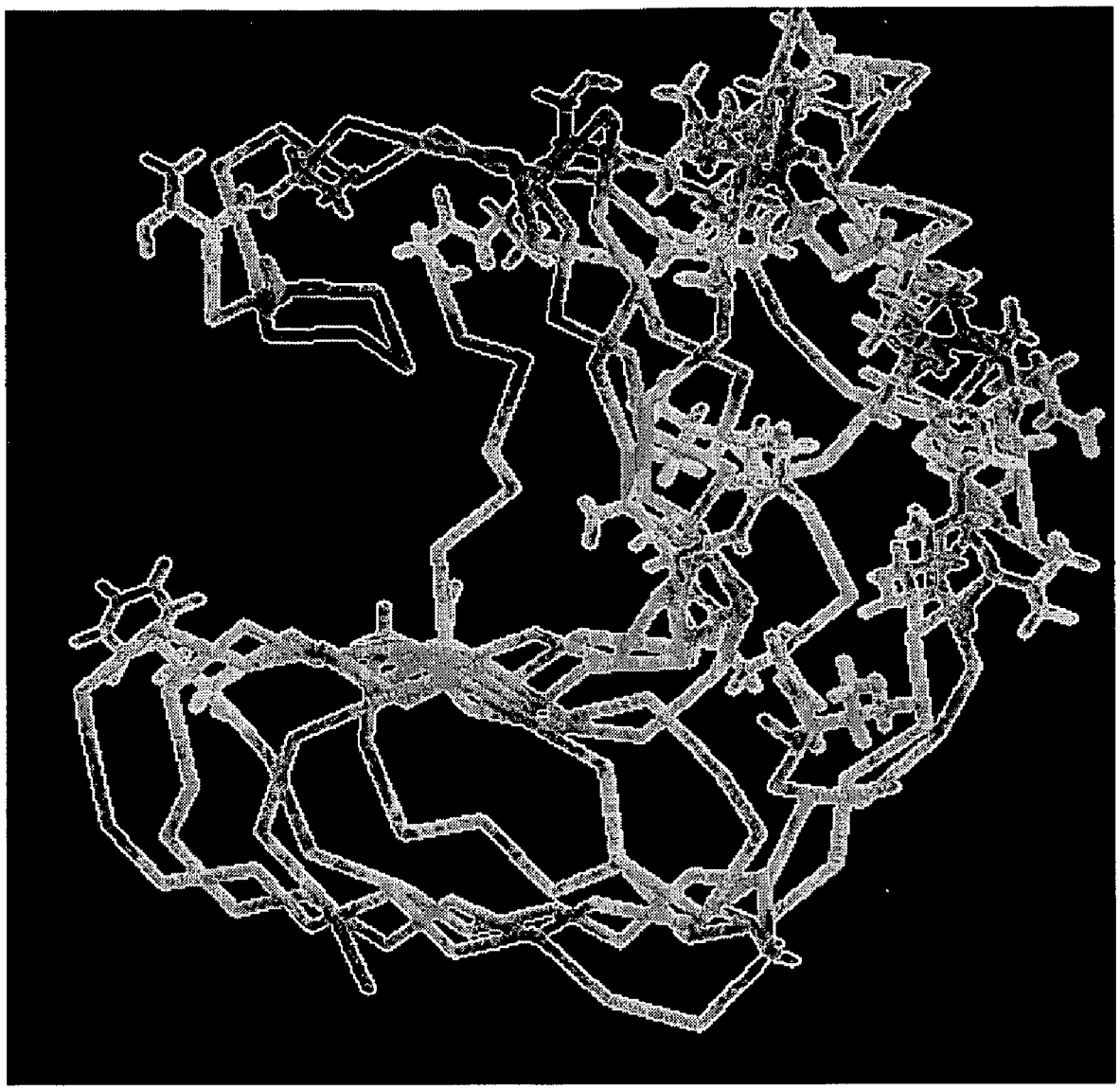
FIG. 9 represents the molecular model of the mutant 14.7% of the *P. griseofulvum* xylanase. The 21 first mutations (shared with the mutant 10%) are in light grey, the additional "structural" mutations in darker grey. Side chains of the "new" residues (the replacement residues) are represented in this figure.

FIG. 9 shows a 3-D picture from which it can be derived where in the enzyme structure modifications were made. Side chains are given for the replacement residues. There is a perfect fit with the WT model (see FIG. 10). For sequence alignments, see FIG. 8.

EXAMPLE 12

A Sequence about 84.3% Homologous (Identical) to SEQ ID NO: 11

Construction of a Model with about 15.7% Random Mutations

A new sequence about 84.3% homologous (identical) to the wild type sequence has been designed by selecting random mutations as derivable from a Blast retrieval and a clustalW alignment with the sequence of *P. griseofulvum* family 11 xylanase as a query.

In Table 7 the random mutations that were selected are shown in bold and italic. Where no bold and italic residue is indicated, the residue of the *P. griseofulvum* xylanase remained unchanged. Amino acid positions referred to are those in the mature enzyme. For an explanation of the column headings, see above.

A new molecular model of the *P. griseofulvum* xylanase has been built based on this mutated sequence (using xyo.pdb as template). It was performed following the same strategy as described for the model of the wild type.

Based on this list of mutations, 10 models were generated. Modeler and Procheck analysis revealed that all of them were of good quality, model number 10 being slightly better than the other ones. None of the side chain residues of model 10 were out of the Ramachandran Plot. Once again, no volumic clashes were observed despite the high % of mutations.

A Blast retrieval made with the sequence about 84.3% homologous to SEQ ID NO: 11 has revealed 70% of identity with Xyn1 *T. reesei* (Torronen A et al. 1992 *Biotechnology* (N.Y.) 10: 1461-1465). By way of comparison, the family 11 xylanase found to be closest to SEQ ID NO: 11—the xylanase from *Penicillium* sp.40 (Kimura et al. 2000 *Biosci. Biotechnol. Biochem.* 64:1230-1237)—has 77% sequence identity with SEQ ID NO: 11. The sequence about 84.3% identical to SEQ ID NO: 11 is referred to as the M3P sequence having SEQ ID NO: 17. The sequence identities given in this paragraph are the % sequence identity over the length of the mature enzyme.

TABLE 7

| In A160 | In 1XY0 | Other possibilities | comments |
|---|---|---|---|
| A32 | G | *N* | |
| K40 | *S* | T, V, Q, E, A, R | End of sheet, not conserved |
| N41 | — | D | Low security, highly conserved |
| S44 | *N* | | Begin of sheet, active site vicinity |
| A52 | *Q* | N, S | |
| T53 | *P* | N | |
| S55 | *K* | N, A, G | |
| A56 | N | *R*, T, S | |
| R57 | *K* | Q, H, R | |
| N58 | V | *D*, T, A | |
| E94 | T | *D*, S | |
| S100 | *G* | | |
| M101 | *A* | L, G | |
| T102 | — | Q, E, S | |
| F103 | *K* | Y | |
| K104 | *L* | R, M | |
| T106 | *E* | Q, S | |
| V107 | — | F, L | Hydrophobic Interaction with A 158 |
| T108 | — | N, Q, E | Y or K less accepted |
| S109 | — | *T* | Q not possible |
| S112 | — | *G* | |
| V113 | — | *T* | |
| S129 | *G* | | |
| S131 | *T* | | |
| S132 | A | *K*, R | |
| I140 | *V* | | |
| R142 | — | *Q*, T | |
| N143 | — | *S*, E, Q | Low security K144 and R145 highly conserved |
| K144 | *H* | | Highly conserved |
| R145 | — | | Interaction E90 Strictly conserved |
| S146 | — | T, V | Highly conserved |
| S147 | — | G | Highly conserved |
| L162 | *Q* | Y, A, H | |
| M164 | *L* | | |
| L166 | — | M | |
| S168 | *T* | N | |
| Q180 | F | K, *E* | |

The above demonstrates that multiple amino acid substitutions are possible in SEQ ID NO: 11 without effect on the structure or functionality of the enzyme. SEQ ID NOs: 15-18 are only a few examples of the many variant forms of SEQ ID NO: 11 that can be created (and tested) by those skilled in the art. FIG. 8 represents a sequence alignment of SEQ ID NOs: 15-17. FIG. 10 shows the perfect fit of the Models 10% and 14.7% with the 3D-structure 1XYO. Example 12 shows that similar results can be obtained using another model and with other modifications to SEQ ID NO: 11.

The applicant has made a deposit of microorganism for the strain *Penicillium griseofulvum* Diercks A160 according to the invention under the deposit number MUCL 41920 on Dec. 13, 1999 at the BCCM/MUCL Culture Collection (Mycothèque de l'Université Catholique de Louvain, Place de la Croix du Sud 3, B-1348 LOUVAIN-LA-NEUVE, BELGIUM) and the deposit of the microorganism *Escherichia coli* DH10B (pPGXYNA) according to the invention on Dec. 13, 1999 under the deposit number LMBP 3987 at the Laboratorium voor Moleculaire Biologie BCCM/LMBP (K.L. Ledeganckstraat 35, B-9000 GENT, BELGIUM).

While the present invention has been described in some detail for purposes of clarity and understanding, one skilled in the art will appreciate that various changes in form and detail can be made without departing from the true scope of the invention. All figures, tables, and listings, as well as publications, referred to above, are hereby incorporated by reference.

What is claimed is:

1. An isolated or purified enzyme with xylanolytic activity having more than 85% sequence identity with the amino acid sequence of SEQ ID NO: 11, or with the mature enzyme having the amino acid sequence of SEQ ID NO: 11 wherein the first 27 amino acids have been deleted.

2. The enzyme of claim 1, having more than 90% sequence identity with the amino acid sequence of SEQ ID NO: 11.

3. The enzyme of claim 1, having more than 90% sequence identity with the mature enzyme.

4. The enzyme of claim 1, which wherein said enzyme is a family 11 xylanase.

5. The enzyme of claim 1, wherein one or more of the amino acids of SEQ ID NO: 11 have been modified.

6. The enzyme of claim 1, wherein 5, 10, 13, or up to 15%, of the amino acids of SEQ ID NO: 11 have been modified.

7. The enzyme of claim 5, wherein said modification is a deletion, an insertion and/or a substitution.

8. The enzyme of claim 7, wherein said modification is a substitution.

9. The enzyme of claim 8, wherein said substitution is a conservative substitution.

10. The enzyme of claim 8, wherein said substitution is a neutral substitution.

11. The enzyme of claim 7, wherein the first 8 amino acids of SEQ ID NO: 11 have been deleted.

12. The enzyme of claim 5, wherein the following are not modified: the first 30 amino acids at the N-terminal part of the mature enzyme, the Ser44, the three putative CK2-Phospho sites (at residues 3-6, 112-115, 132-135), the nine putative myristyl N-myristoylation sites, the putative N-glycosilation site (at residues 60-63) and the putative CAMP-Phospho site (at residues 144-147).

13. The enzyme of claim 1, having one or more amino acid substitutions at one or more of the following positions in the mature enzyme: 32, 40, 41, 44, 52, 53, 55, 56, 57, 58, 94, 100, 101, 102, 103, 104, 106, 107, 108, 109, 112, 113, 129, 131, 132, 140, 142, 143, 144, 145, 146, 147, 162, 164, 166, 168 or 180.

14. The enzyme of claim 1, comprising the amino acid sequence of SEQ ID NO: 11, SEQ ID NO: 15, SEQ ID NO: 16, SEQ ID NO: 17 or SEQ ID NO: 18.

15. The enzyme of claim 1, having the amino acid sequence selected from the group consisting of:
  any of SEQ ID NO: 11, 15, 16, 18, having further a deletion of the first 8 amino acids;
  any of SEQ ID NO: 11, 15, 16, 18 having further a deletion of the first 27 amino acids; and
  SEQ ID NO: 11 having one or more amino acid substitutions at one or more of the following positions in the mature enzyme: 32, 40, 41, 44, 52, 53, 55, 56, 57, 58, 94, 100, 101, 102, 103, 104, 106, 107, 108, 109, 112, 113, 129, 131, 132, 140, 142, 143, 144, 145, 146, 147, 162, 164, 166, 168, or 180.

16. The enzyme of claim 1, wherein said enzyme has xylanolytic activity at a pH between 4.5 and 7.0 and optimum xylanolytic activity at a temperature between 35 and 55° C.

17. The enzyme of claim 1, wherein said enzyme comprises SEQ ID NO: 1.

18. The enzyme of claim 1, wherein the enzyme is a *Penicillium* enzyme.

19. The enzyme of claim 1, wherein the enzyme is a *Penicillium griseofulvum* enzyme.

20. An isolated or purified protein with xylanolytic activity comprising the amino acid sequence of SEQ ID NO: 11, SEQ ID NO: 15, SEQ ID NO: 16, SEQ ID NO: 17, SEQ ID NO: 18, or an amino acid sequence having more than 85% identity to SEQ ID NO: 11.

21. A solid support having a fixed element that comprises the enzyme with xylanolytic activity of claim 1.

22. The solid support of claim 21 to which the isolated or purified enzyme with xylanolytic activity is fixed.

23. A method for the degradation of plant cell wall components comprising adding the enzyme of claim 1 to said plant cell wall components.

24. A method for the decomposition of plants and fruits comprising adding the enzyme of claim 1 to the preparation processes of fruit, legume juices, beer, paper, starch, gluten or vegetable oil.

25. A method for the decomposition of wastes comprising adding the enzyme of claim 1 to waste materials such as agricultural wastes or wastes from paper mills.

26. A method for increasing the volume of baked products comprising adding the enzyme of claim 1 to said baked products before baking.

27. A method for the separation of starch and gluten comprising adding the enzyme of claim 1 to a batter comprising starch and gluten.

28. An isolated and purified protein with xylanolytic activity having more than 85% identity with the amino acid sequence of SEQ ID NO: 11.

29. The isolated and purified protein of claim 28 having more than 90% identity with the amino acid sequence of SEQ ID NO: 11.

30. The isolated and purified protein of claim 28 having more than 90% identity with the amino acid sequence of SEQ ID NO: 11, wherein the first 27 amino acids have been deleted therefrom.

31. The isolated and purified protein of claim 28 having an amino acid sequence selected from the group consisting of:
  SEQ ID NO: 11;
  SEQ ID NO: 15;
  SEQ ID NO: 16;
  SEQ ID NO: 17;
  SEQ ID NO: 18;
  any of SEQ ID NO: 11, 15, 16, 18, having further a deletion of the first 8 amino acids; and
  any of SEQ ID NO: 11, 15, 16, 18 having further a deletion of the first 27 amino acids.

* * * * *

UNITED STATES PATENT AND TRADEMARK OFFICE
CERTIFICATE OF CORRECTION

PATENT NO. : 7,998,720 B2  
APPLICATION NO. : 11/418376  
DATED : August 16, 2011  
INVENTOR(S) : Jean-Luc Jonniaux and Thierry Dauvrin Page 1 of 1

It is certified that error appears in the above-identified patent and that said Letters Patent is hereby corrected as shown below:

On the Title Page:

Item (56), line 12, please delete "Purificaiton," and insert therefore, --Purification,--.

Item (56), line 13, please delete "sylanase" and insert therefore, --xylanase--.

Item (56), line 13, please delete "penicilium" and insert therefore, --penicillium--.

Item (56), line 55, please delete "Crystalllographic" and insert therefore, --Crystallographic--.

At column 6, line 57, please delete "glycosilation" and insert therefore, --glycosylation--.

At column 8, line 7, please delete "ampicilline." and insert therefore, --ampicillin.--.

At column 10, line 67, please delete "the" and insert therefore, --The--.

At column 12, line 53, please delete "J" and insert therefore, --J.--.

At column 16, approximately line 19, please delete "Sherzyme™" and insert therefore, --Shearzyme™--.

At column 16, line 58, please delete "that that" and insert therefore, --that--.

At column 20, line 15, please delete "J" and insert therefore, --J.--.

At column 20, line 66, please delete "Glu 177" and insert therefore, --Glu177--.

At column 21, line 13, please delete "glycosilation" and insert therefore, --glycosylation--.

At column 21, line 17-18, please delete "glycosilation" and insert therefore, --glycosylation--.

At column 21, line 24, please delete "J" and insert therefore, --J.--.

At column 21, line 32, please delete "and or" and insert therefore, --and/or--.

At column 21, approximately line 29, please delete "Based of" and insert therefore, --Based on--.

At column 55, line 62, after "1," please delete "which".

At column 57, line 1, please delete "glycosilation" and insert therefore, --glycosylation--.

Signed and Sealed this  
Eighth Day of May, 2012

David J. Kappos  
*Director of the United States Patent and Trademark Office*

SEQUENCE LISTING

```
<160> NUMBER OF SEQ ID NOS: 29

<210> SEQ ID NO 1
<211> LENGTH: 28
<212> TYPE: PRT
<213> ORGANISM: Penicillium griseofulvum
<220> FEATURE:
<221> NAME/KEY: Variant
<222> LOCATION: (1)..(26)
<223> OTHER INFORMATION: Xaa = Any Amino Acid

<400> SEQUENCE: 1

Asp Ile Thr Gln Asn Glu Arg Gly Thr Asn Asn Gly Tyr Phe Tyr Ser
1               5                   10                  15

Phe Trp Thr Xaa Ala Ala Gly Gly Gly Asn Val Tyr
            20                  25

<210> SEQ ID NO 2
<211> LENGTH: 23
<212> TYPE: DNA
<213> ORGANISM: Artificial
<220> FEATURE:
<223> OTHER INFORMATION: Degenerate primers based on N-terminal amino
      acid sequence

<400> SEQUENCE: 2
ggytayttyt ayaayttytg gac                                              23

<210> SEQ ID NO 3
<211> LENGTH: 23
<212> TYPE: DNA
<213> ORGANISM: Artificial
<220> FEATURE:
<223> OTHER INFORMATION: Degenerate primers based on N-terminal amino
      acid sequence

<400> SEQUENCE: 3
ggytaytayt aytcrttytg gac                                              23

<210> SEQ ID NO 4
<211> LENGTH: 17
<212> TYPE: DNA
<213> ORGANISM: Artificial
<220> FEATURE:
<223> OTHER INFORMATION: Hypothetical degenerate sequence

<400> SEQUENCE: 4
tcgacraygt agtaytc                                                     17

<210> SEQ ID NO 5
```

```
<211> LENGTH: 102
<212> TYPE: DNA
<213> ORGANISM: Penicillium griseofulvum
<220> FEATURE:
<221> NAME/KEY: misc_feature
<222> LOCATION: (1)..(102)
<223> OTHER INFORMATION: n = A, T, C or G

<400> SEQUENCE: 5
cnagtacaac aacgnnaagn ccggcnaata cagngtgnan tggaagaact gcggntattt      60
cacctctggc aagggctgga nnactggtag ngcccggtaa gt                        102

<210> SEQ ID NO 6
<211> LENGTH: 87
<212> TYPE: DNA
<213> ORGANISM: Penicillium griseofulvum
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t

<400> SEQUENCE: 6
cggcnaatac aagggtgtna ntggaagaac tgcggnnatt tcacctcngg caagggctgg      60
actactggta gtgcccggta agtgcaa                                          87

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7
tatttcacct ctggcaaggg ct                                               22

<210> SEQ ID NO 8
<211> LENGTH: 2225
<212> TYPE: DNA
<213> ORGANISM: Penicillium griseofulvum
<220> FEATURE:
<221> NAME/KEY: misc_feature
<222> LOCATION: (1)..(2225)
<223> OTHER INFORMATION: n = A, T, C or G
<220> FEATURE:
<221> NAME/KEY: exon
<222> LOCATION: (962)..(1213)
<220> FEATURE:
<221> NAME/KEY: Intron
<222> LOCATION: (1214)..(1261)
<220> FEATURE:
<221> NAME/KEY: exon
<222> LOCATION: (1264)..(1662)

<400> SEQUENCE: 8
gaattctgct ttgccaagnt tcaacgcgga gactcacagt cacattcttc gaatcttctt      60
```

```
ggcacgtgtt cttgggtcct tcgagaaatc atggatctgg aaagttaacc agtaagccgg    120
ttagaagacc cggatcagcg acaaatagcc ggtagtaaat tacttaatcg tatcgctaga    180
tctgatcatc cgatagacaa acaaacaaac ttaggctacc ctagagatga atcatgacag    240
tagactattt taccaaggaa tatttagaac aagcataccc ctcactaatt gggttgacta    300
tataaatacg gttaaaagca tgggggactt tcccaaggtt gttcctgcca agctttgaga    360
tatacacccg ttgatccatg gatcaccgag gttgtccctg agctgtctca agcttacaac    420
aacttccaag gttctccaat gtcttatgag agctgataat cgaaataaga tcaagtagcc    480
gatgtttccc cggcttttaa actgcctgat cttgggttta gcctggccaa gctacatcca    540
ttatagccgt gatgaatttc cccgcattta cacagccggt ggctgaagtg tgcaacatgc    600
ttatttttac ttgaagaagt ttagccgact caatagtttc tacatgctta tttagctact    660
aaaatctgat tttagcctgg ttggatgata tagggatata gctgtcggtc cgatggacca    720
gtaatagttc atggacagtg aacatgaccc gtgtttaacg tataattagt gcaattggaa    780
cagggcaagg ggataaatag gtcgttggct aaattcattc gagacatgtg gaggactatg    840
aaactgttta aactcgcccc acaccctccg tcaatataaa agaggtcttc tccccaagga    900
atcatccatc acaaaacaca ctccaattca ttcctcaatt accagcatct gacctttcat    960
``` a atg gtc tct ttc tca agc ctc ttt gtc gct gca tgc gcc gct gtc agt    1009
  Met Val Ser Phe Ser Ser Leu Phe Val Ala Ala Cys Ala Ala Val Ser
   1          5              10             15 gcc ctc gcg ctt ccc agt gac gtg gaa aag cgc gac atc acc cag aac    1057
Ala Leu Ala Leu Pro Ser Asp Val Glu Lys Arg Asp Ile Thr Gln Asn
        20              25             30 gag cga gga acc aac ggc ggc tac ttc tac tct ttc tgg acc aac ggt    1105
Glu Arg Gly Thr Asn Gly Gly Tyr Phe Tyr Ser Phe Trp Thr Asn Gly
     35             40            45 ggc ggc agt gtc tcc tac aac aac ggc aat gca ggc caa tac agt gtc    1153
Gly Gly Ser Val Ser Tyr Asn Asn Gly Asn Ala Gly Gln Tyr Ser Val
    50              55            60 aac tgg aag aat tgc gga tct ttc acc tct ggc aag ggc tgg gct aca    1201
Asn Trp Lys Asn Cys Gly Ser Phe Thr Ser Gly Lys Gly Trp Ala Thr
65           70             75            80 ggt agc gcc cgg taagtccaga caacatactc aatattgata aatacttacg    1253
Gly Ser Ala Arg tcgtgttaga aac atc aac ttt tcc gga aat ttc aat ccc tcc gga aat    1302
            Asn Ile Asn Phe Ser Gly Asn Phe Asn Pro Ser Gly Asn
             85             90            95 gct tac ctg gct gtc tac ggc tgg acc aag ggc ccc ctc gtt gag tac    1350
Ala Tyr Leu Ala Val Tyr Gly Trp Thr Lys Gly Pro Leu Val Glu Tyr
    100             105           110 tac atc atg gaa aac tat ggc gaa tac aac cca ggc ggc agc atg acc    1398
Tyr Ile Met Glu Asn Tyr Gly Glu Tyr Asn Pro Gly Gly Ser Met Thr
    115             120           125 ttc aag gga aca gta acc agc gat ggg tcc gtc tat gat atc tac aag    1446
Phe Lys Gly Thr Val Thr Ser Asp Gly Ser Val Tyr Asp Ile Tyr Lys
130           135           140          145 cat act cag gtc aac cag cct tcg atc att tcg gat tct agc acc ttc    1494
His Thr Gln Val Asn Gln Pro Ser Ile Ile Ser Asp Ser Ser Thr Phe
         150            155           160 gac cag tac tgg tct atc cgt cgg aac aag cgt agc agt gga act gtc    1542
Asp Gln Tyr Trp Ser Ile Arg Arg Asn Lys Arg Ser Ser Gly Thr Val
        165           170           175 act act ggt aac cac ttc aat gct tgg gct aag ctt gga atg ggt ctt    1590
Thr Thr Gly Asn His Phe Asn Ala Trp Ala Lys Leu Gly Met Gly Leu

|  |  |  |  | 180 |  |  |  | 185 |  |  |  | 190 |  |  |  |
|---|---|---|---|---|---|---|---|---|---|---|---|---|---|---|---|
| gga | tct | cac | gac | tac | cag | att | gtt | aac | act | gag | ggt | tac | caa | agc | agt | 1638 |
| Gly | Ser | His | Asp | Tyr | Gln | Ile | Val | Asn | Thr | Glu | Gly | Tyr | Gln | Ser | Ser |
|  |  | 195 |  |  |  |  | 200 |  |  |  |  | 205 |  |  |  |

| gga | tct | gca | acc | atc | act | gtt | tca | taagcgtgtg aatccctgc agtggtttca | 1692 |
|---|---|---|---|---|---|---|---|---|---|
| Gly | Ser | Ala | Thr | Ile | Thr | Val | Ser |  |  |
| 210 |  |  |  | 215 |  |  |  |  |  |

```
tgcgaaatgt cacttgctgc tagcaagggt ttggaagagc tattgttatg aacctgttaa      1752
ctgtatatgg agcaaagttg tgtaccgata cttcacttca atccggttca tcgggtgttt      1812
agcttgttgg tcttctcttg gatatttgcc ttgttaggaa tcaatccata tttacgcccc      1872
aaatttaagt ttctaggagt atccacaggt gcttgcctta gtatgtttca gcctgcggag      1932
tagtagtttc taacaaaagt aatgagatgc gatgtctatt ttgaaaattg catgtcgcac      1992
ctatatgcag atactaaaaa gcatgtcaca agtggctata tatcgacaat agtggttagt      2052
atatcaccgt tcctaaaagt gcatttcgca taactcacat tctgttgggg atcagtgaaa      2112
ccacaactag gcccactact tttcttcggt atcttcccga acttcttacg cccgctaagc      2172
ggcgccttgt cgccaacgg atacccatac caaaaccacc aacttggggg gga             2225

<210> SEQ ID NO 9
<211> LENGTH: 251
<212> TYPE: DNA
<213> ORGANISM: Penicillium griseofulvum
<220> FEATURE:
<221> NAME/KEY: misc_feature
<222> LOCATION: (1)..(84)
<223> OTHER INFORMATION: CDS for exon 1

<400> SEQUENCE: 9
atggtctctt tctcaagcct ctttgtcgct gcatgcgccg ctgtcagtgc cctcgcgctt       60
cccagtgacg tggaaaagcg cgacatcacc cagaacgagc gaggaaccaa cggcggctac      120
ttctactctt tctggaccaa cggtggcggc agtgtctcct acaacaacgg caatgcaggc      180
caatacagtg tcaactggaa gaattgcgga tctttcacct ctggcaaggg ctgggctaca      240
ggtagcgccc g                                                           251

<210> SEQ ID NO 10
<211> LENGTH: 400
<212> TYPE: DNA
<213> ORGANISM: Penicillium griseofulvum
<220> FEATURE:
<221> NAME/KEY: misc_feature
<222> LOCATION: (1)..(133)
<223> OTHER INFORMATION: CDS for exon 2

<400> SEQUENCE: 10
aaacatcaac ttttccggaa atttcaatcc ctccggaaat gcttacctgg ctgtctacgg       60
ctggaccaag ggccccctcg ttgagtacta catcatggaa actatggcg aatacaaccc      120
aggcggcagc atgaccttca agggaacagt aaccagcgat gggtccgtct atgatatcta      180
caagcatact caggtcaacc agccttcgat catttcggat tctagcacct tcgaccagta      240
ctggtctatc cgtcggaaca agcgtagcag tggaactgtc actactggta accacttcaa      300
tgcttgggct aagcttggaa tgggtcttgg atctcacgac taccagattg ttaacactga      360
gggttaccaa agcagtggat ctgcaaccat cactgtttca                            400

<210> SEQ ID NO 11
<211> LENGTH: 217
<212> TYPE: PRT
```

```
<213> ORGANISM: Penicillium griseofulvum
<220> FEATURE:
<221> NAME/KEY: MISC_FEATURE
<223> OTHER INFORMATION: WT sequence
<220> FEATURE:
<221> NAME/KEY: SIGNAL
<222> LOCATION: (1)..(27)
<223> OTHER INFORMATION: Signal sequence driving secretion of the enzyme

<400> SEQUENCE: 11

Met Val Ser Phe Ser Ser Leu Phe Val Ala Ala Cys Ala Ala Val Ser
 1               5                  10                  15

Ala Leu Ala Leu Pro Ser Asp Val Glu Lys Arg Asp Ile Thr Gln Asn
            20                  25                  30

Glu Arg Gly Thr Asn Gly Gly Tyr Phe Tyr Ser Phe Trp Thr Asn Gly
        35                  40                  45

Gly Gly Ser Val Ser Tyr Asn Asn Gly Asn Ala Gly Gln Tyr Ser Val
    50                  55                  60

Asn Trp Lys Asn Cys Gly Ser Phe Thr Ser Gly Lys Gly Trp Ala Thr
65                  70                  75                  80

Gly Ser Ala Arg Asn Ile Asn Phe Ser Gly Asn Phe Asn Pro Ser Gly
                85                  90                  95

Asn Ala Tyr Leu Ala Val Tyr Gly Trp Thr Lys Gly Pro Leu Val Glu
            100                 105                 110

Tyr Tyr Ile Met Glu Asn Tyr Gly Glu Tyr Asn Pro Gly Gly Ser Met
        115                 120                 125

Thr Phe Lys Gly Thr Val Thr Ser Asp Gly Ser Val Tyr Asp Ile Tyr
    130                 135                 140

Lys His Thr Gln Val Asn Gln Pro Ser Ile Ile Ser Asp Ser Thr
145                 150                 155                 160

Phe Asp Gln Tyr Trp Ser Ile Arg Arg Asn Lys Arg Ser Ser Gly Thr
                165                 170                 175

Val Thr Thr Gly Asn His Phe Asn Ala Trp Ala Lys Leu Gly Met Gly
            180                 185                 190

Leu Gly Ser His Asp Tyr Gln Ile Val Asn Thr Glu Gly Tyr Gln Ser
        195                 200                 205

Ser Gly Ser Ala Thr Ile Thr Val Ser
    210                 215

<210> SEQ ID NO 12
<211> LENGTH: 24
<212> TYPE: DNA
<213> ORGANISM: Artificial
<220> FEATURE:
<223> OTHER INFORMATION: Synthetic oligonucleotide

<400> SEQUENCE: 12
ggaattccat aatggtctct ttct                                    24

<210> SEQ ID NO 13
<211> LENGTH: 25
<212> TYPE: DNA
<213> ORGANISM: Artificial
<220> FEATURE:
<223> OTHER INFORMATION: Synthetic oligonucleotide

<400> SEQUENCE: 13
gctctagagc cacttgtgac atgct                                   25

<210> SEQ ID NO 14
<211> LENGTH: 6
```

```
<212> TYPE: PRT
<213> ORGANISM: Artificial sequence
<220> FEATURE:
<223> OTHER INFORMATION: Conserved amino acid sequence from the family
      G xylanases

<400> SEQUENCE: 14

Glu Tyr Tyr Ile Val Asp
1               5

<210> SEQ ID NO 15
<211> LENGTH: 217
<212> TYPE: PRT
<213> ORGANISM: Artificial Sequence
<220> FEATURE:
<221> NAME/KEY: misc_feature
<223> OTHER INFORMATION: M1P sequence
<220> FEATURE:
<221> NAME/KEY: misc_feature
<223> OTHER INFORMATION: M1P sequence
<220> FEATURE:
<221> NAME/KEY: SIGNAL
<222> LOCATION: (1)..(27)

<400> SEQUENCE: 15

Met Val Ser Phe Ser Ser Leu Phe Val Ala Ala Cys Ala Ala Val Ser
1               5                   10                  15

Ala Leu Ala Leu Pro Ser Asp Val Glu Lys Arg Asp Ile Thr Gln Asn
            20                  25                  30

Glu Arg Gly Thr Asn Gly Gly Tyr Phe Tyr Ser Phe Trp Thr Asn Gly
        35                  40                  45

Gly Gly Ser Val Ser Tyr Asn Asn Gly Asn Gly Gln Tyr Ser Val
    50                  55                  60

Asn Trp Lys Asn Cys Gly Ser Phe Thr Ser Gly Lys Gly Trp Gln Pro
65                  70                  75                  80

Gly Lys Asn Lys Val Ile Asn Phe Ser Gly Asn Phe Asn Pro Ser Gly
                85                  90                  95

Asn Ala Tyr Leu Ala Val Tyr Gly Trp Thr Lys Gly Pro Leu Val Glu
            100                 105                 110

Tyr Tyr Ile Met Glu Asn Tyr Gly Thr Tyr Asn Pro Gly Gly Gly Ala
        115                 120                 125

Thr Lys Leu Gly Glu Val Thr Ser Asp Gly Ser Val Tyr Asp Ile Tyr
    130                 135                 140

Lys His Thr Gln Val Asn Gln Pro Ser Ile Ile Ser Asp Thr Ala Thr
145                 150                 155                 160

Phe Asp Gln Tyr Trp Ser Val Arg Arg Asn His Arg Ser Ser Gly Thr
                165                 170                 175

Val Thr Thr Gly Asn His Phe Asn Ala Trp Ala Lys Gln Gly Leu Gly
            180                 185                 190

Leu Gly Thr His Asp Tyr Gln Ile Val Asn Thr Glu Gly Tyr Phe Ser
        195                 200                 205

Ser Gly Ser Ala Thr Ile Thr Val Ser
    210                 215

<210> SEQ ID NO 16
<211> LENGTH: 217
<212> TYPE: PRT
<213> ORGANISM: Artificial Sequence
<220> FEATURE:
<221> NAME/KEY: misc_feature
<223> OTHER INFORMATION: M2P sequence
<220> FEATURE:
<221> NAME/KEY: misc_feature
```

<223> OTHER INFORMATION: M2P sequence

<400> SEQUENCE: 16

```
Met Val Ser Phe Ser Ser Leu Phe Val Ala Ala Cys Ala Ala Val Ser
1               5                   10                  15

Ala Leu Ala Leu Pro Ser Asp Val Glu Lys Arg Asp Ile Thr Gln Asn
            20                  25                  30

Glu Arg Gly Thr Asn Gly Gly Tyr Phe Tyr Ser Phe Trp Thr Asn Gly
        35                  40                  45

Gly Gly Ser Val Ser Tyr Asn Asn Gly Asn Gly Gln Tyr Ser Val
    50                  55                  60

Asn Trp Lys Asn Cys Gly Ser Phe Thr Ser Gly Lys Gly Trp Gln Pro
65                  70                  75                  80

Gly Lys Asn Lys Val Ile Asn Phe Ser Gly Asn Phe Asn Pro Ser Gly
                85                  90                  95

Asn Ala Tyr Leu Ala Val Tyr Gly Trp Thr Lys Gly Pro Leu Val Glu
            100                 105                 110

Tyr Tyr Ile Met Glu Asn Tyr Gly Thr Tyr Asn Pro Gly Gly Gly Ala
        115                 120                 125

Ser Lys Leu Gly Glu Leu Thr Thr Asp Gly Ala Val Tyr Asp Ile Tyr
    130                 135                 140

Lys His Thr Gln Val Asn Gln Pro Ser Ile Ile Gly Asp Thr Ala Thr
145                 150                 155                 160

Phe Asp Gln Tyr Trp Ser Val Arg Arg Asn His Arg Ser Ser Gly Thr
                165                 170                 175

Val Thr Thr Gly Asn His Phe Asn Ala Trp Ala Lys Gln Gly Leu Gly
            180                 185                 190

Met Gly Thr His Asp Tyr Gln Ile Val Asn Thr Glu Gly Tyr Phe Ser
        195                 200                 205

Ser Gly Ser Ala Thr Ile Thr Val Ser
    210                 215
```

<210> SEQ ID NO 17
<211> LENGTH: 217
<212> TYPE: PRT
<213> ORGANISM: Artificial Sequence
<220> FEATURE:
<221> NAME/KEY: misc_feature
<223> OTHER INFORMATION: M3P sequence

<400> SEQUENCE: 17

```
Met Val Ser Phe Ser Ser Leu Phe Val Ala Ala Cys Ala Ala Val Ser
1               5                   10                  15

Ala Leu Ala Leu Pro Ser Asp Val Glu Lys Arg Asp Ile Thr Gln Asn
            20                  25                  30

Glu Arg Gly Thr Asn Gly Gly Tyr Phe Tyr Ser Phe Trp Thr Asn Gly
        35                  40                  45

Gly Gly Ser Val Ser Tyr Asn Asn Gly Asn Gly Gln Tyr Ser Val
    50                  55                  60

Asn Trp Ser Asn Cys Gly Asn Phe Thr Ser Gly Lys Gly Trp Gln Pro
65                  70                  75                  80

Gly Lys Arg Lys Asp Ile Asn Phe Ser Gly Asn Phe Asn Pro Ser Gly
                85                  90                  95

Asn Ala Tyr Leu Ala Val Tyr Gly Trp Thr Lys Gly Pro Leu Val Glu
            100                 105                 110

Tyr Tyr Ile Met Glu Asn Tyr Gly Asp Tyr Asn Pro Gly Gly Gly Ala
        115                 120                 125
```

```
Thr Lys Leu Gly Glu Val Asn Thr Asp Gly Gly Thr Tyr Asp Ile Tyr
    130                 135                 140

Lys His Thr Gln Val Asn Gln Pro Ser Ile Ile Gly Asp Thr Lys Thr
145                 150                 155                 160

Phe Asp Gln Tyr Trp Ser Val Arg Gln Ser His Arg Ser Ser Gly Thr
                165                 170                 175

Val Thr Thr Gly Asn His Phe Asn Ala Trp Ala Lys Gln Gly Leu Gly
            180                 185                 190

Leu Gly Thr His Asp Tyr Gln Ile Val Asn Thr Glu Gly Tyr Glu Ser
        195                 200                 205

Ser Gly Ser Ala Thr Ile Thr Val Ser
    210                 215
```

```
<210> SEQ ID NO 18
<211> LENGTH: 217
<212> TYPE: PRT
<213> ORGANISM: Artificial Sequence
<220> FEATURE:
<221> NAME/KEY: misc_feature
<222> LOCATION: (59)..(59)
<223> OTHER INFORMATION: Xaa = A, G or N
<220> FEATURE:
<221> NAME/KEY: misc_feature
<222> LOCATION: (67)..(67)
<223> OTHER INFORMATION: Xaa = K, S, T, V, Q, E, A or R
<220> FEATURE:
<221> NAME/KEY: misc_feature
<222> LOCATION: (68)..(68)
<223> OTHER INFORMATION: Xaa = N or D
<220> FEATURE:
<221> NAME/KEY: misc_feature
<222> LOCATION: (71)..(71)
<223> OTHER INFORMATION: Xaa = S or N
<220> FEATURE:
<221> NAME/KEY: misc_feature
<222> LOCATION: (79)..(79)
<223> OTHER INFORMATION: Xaa = A, Q, N or S
<220> FEATURE:
<221> NAME/KEY: misc_feature
<222> LOCATION: (80)..(80)
<223> OTHER INFORMATION: Xaa = T, P or N
<220> FEATURE:
<221> NAME/KEY: misc_feature
<222> LOCATION: (82)..(82)
<223> OTHER INFORMATION: Xaa = S, K, N, A or G
<220> FEATURE:
<221> NAME/KEY: misc_feature
<222> LOCATION: (83)..(83)
<223> OTHER INFORMATION: Xaa = A, N, R, T or S
<220> FEATURE:
<221> NAME/KEY: misc_feature
<222> LOCATION: (84)..(84)
<223> OTHER INFORMATION: Xaa = R, K, Q, H or R
<220> FEATURE:
<221> NAME/KEY: misc_feature
<222> LOCATION: (85)..(85)
<223> OTHER INFORMATION: Xaa = N, V, D, T or A
<220> FEATURE:
<221> NAME/KEY: misc_feature
<222> LOCATION: (121)..(121)
<223> OTHER INFORMATION: Xaa = E, T, D or S
<220> FEATURE:
<221> NAME/KEY: misc_feature
<222> LOCATION: (127)..(127)
<223> OTHER INFORMATION: Xaa = S or G
<220> FEATURE:
<221> NAME/KEY: misc_feature
<222> LOCATION: (128)..(128)
<223> OTHER INFORMATION: Xaa = M, A, L or G
<220> FEATURE:
<221> NAME/KEY: misc_feature
<222> LOCATION: (129)..(129)
<223> OTHER INFORMATION: Xaa = T, S, Q or E
```

```
<220> FEATURE:
<221> NAME/KEY: misc_feature
<222> LOCATION: (130)..(130)
<223> OTHER INFORMATION: Xaa = F, K or Y
<220> FEATURE:
<221> NAME/KEY: misc_feature
<222> LOCATION: (131)..(131)
<223> OTHER INFORMATION: Xaa = K, L, R or M
<220> FEATURE:
<221> NAME/KEY: misc_feature
<222> LOCATION: (133)..(133)
<223> OTHER INFORMATION: Xaa = T, E, Q or S
<220> FEATURE:
<221> NAME/KEY: misc_feature
<222> LOCATION: (134)..(134)
<223> OTHER INFORMATION: Xaa = V, L or F
<220> FEATURE:
<221> NAME/KEY: misc_feature
<222> LOCATION: (135)..(135)
<223> OTHER INFORMATION: Xaa = T, Q, E, N or possibly Y or K
<220> FEATURE:
<221> NAME/KEY: misc_feature
<222> LOCATION: (136)..(136)
<223> OTHER INFORMATION: Xaa = S or T
<220> FEATURE:
<221> NAME/KEY: misc_feature
<222> LOCATION: (139)..(139)
<223> OTHER INFORMATION: Xaa = S, A or G
<220> FEATURE:
<221> NAME/KEY: misc_feature
<222> LOCATION: (140)..(140)
<223> OTHER INFORMATION: Xaa = V or T
<220> FEATURE:
<221> NAME/KEY: misc_feature
<222> LOCATION: (156)..(156)
<223> OTHER INFORMATION: Xaa = S or G
<220> FEATURE:
<221> NAME/KEY: misc_feature
<222> LOCATION: (158)..(158)
<223> OTHER INFORMATION: Xaa = S or T
<220> FEATURE:
<221> NAME/KEY: misc_feature
<222> LOCATION: (159)..(159)
<223> OTHER INFORMATION: Xaa = S, A, K or R
<220> FEATURE:
<221> NAME/KEY: misc_feature
<222> LOCATION: (167)..(167)
<223> OTHER INFORMATION: Xaa = I or V
<220> FEATURE:
<221> NAME/KEY: misc_feature
<222> LOCATION: (169)..(169)
<223> OTHER INFORMATION: Xaa = R, T or Q
<220> FEATURE:
<221> NAME/KEY: misc_feature
<222> LOCATION: (170)..(170)
<223> OTHER INFORMATION: Xaa = N, S, E or Q
<220> FEATURE:
<221> NAME/KEY: misc_feature
<222> LOCATION: (171)..(171)
<223> OTHER INFORMATION: Xaa = K or H
<220> FEATURE:
<221> NAME/KEY: misc_feature
<222> LOCATION: (172)..(172)
<223> OTHER INFORMATION: Xaa = R or V
<220> FEATURE:
<221> NAME/KEY: misc_feature
<222> LOCATION: (173)..(173)
<223> OTHER INFORMATION: Xaa = S, T or V
<220> FEATURE:
<221> NAME/KEY: misc_feature
<222> LOCATION: (174)..(174)
<223> OTHER INFORMATION: Xaa = S or G
<220> FEATURE:
<221> NAME/KEY: misc_feature
<222> LOCATION: (189)..(189)
<223> OTHER INFORMATION: Xaa = L, Q, Y, A or H
<220> FEATURE:
<221> NAME/KEY: misc_feature
<222> LOCATION: (191)..(191)
<223> OTHER INFORMATION: Xaa = M or L
```

```
<220> FEATURE:
<221> NAME/KEY: misc_feature
<222> LOCATION: (193)..(193)
<223> OTHER INFORMATION: Xaa = L or M
<220> FEATURE:
<221> NAME/KEY: misc_feature
<222> LOCATION: (195)..(195)
<223> OTHER INFORMATION: Xaa = S, T or N
<220> FEATURE:
<221> NAME/KEY: misc_feature
<222> LOCATION: (207)..(207)
<223> OTHER INFORMATION: Xaa = Q, F, K or E

<400> SEQUENCE: 18

Met Val Ser Phe Ser Ser Leu Phe Val Ala Ala Cys Ala Ala Val Ser
 1               5                  10                  15

Ala Leu Ala Leu Pro Ser Asp Val Glu Lys Arg Asp Ile Thr Gln Asn
             20                  25                  30

Glu Arg Gly Thr Asn Gly Gly Tyr Phe Tyr Ser Phe Trp Thr Asn Gly
         35                  40                  45

Gly Gly Ser Val Ser Tyr Asn Asn Gly Xaa Gly Gln Tyr Ser Val
     50                  55                  60

Asn Trp Xaa Xaa Cys Gly Xaa Phe Thr Ser Gly Lys Gly Trp Xaa Xaa
65                  70                  75                  80

Gly Xaa Xaa Xaa Xaa Ile Asn Phe Ser Gly Asn Phe Asn Pro Ser Gly
                 85                  90                  95

Asn Ala Tyr Leu Ala Val Tyr Gly Trp Thr Lys Gly Pro Leu Val Glu
            100                 105                 110

Tyr Tyr Ile Met Glu Asn Tyr Gly Xaa Tyr Asn Pro Gly Gly Xaa Xaa
            115                 120                 125

Xaa Xaa Xaa Gly Xaa Xaa Xaa Xaa Asp Gly Xaa Xaa Tyr Asp Ile Tyr
130                 135                 140

Lys His Thr Gln Val Asn Gln Pro Ser Ile Ile Xaa Asp Xaa Xaa Thr
145                 150                 155                 160

Phe Asp Gln Tyr Trp Ser Xaa Arg Xaa Xaa Xaa Xaa Xaa Xaa Gly Thr
                165                 170                 175

Val Thr Thr Gly Asn His Phe Asn Ala Trp Ala Lys Xaa Gly Xaa Gly
            180                 185                 190

Xaa Gly Xaa His Asp Tyr Gln Ile Val Asn Thr Glu Gly Tyr Xaa Ser
            195                 200                 205

Ser Gly Ser Ala Thr Ile Thr Val Ser
        210                 215

<210> SEQ ID NO 19
<211> LENGTH: 179
<212> TYPE: PRT
<213> ORGANISM: Artificial Sequence
<220> FEATURE:
<223> OTHER INFORMATION: consensus sequence

<400> SEQUENCE: 19

Ala Gly Gly Tyr Tyr Tyr Ser Asn Trp Thr Asp Gly Gly Thr Val
 1               5                  10                  15

Thr Tyr Leu Asn Ser Gly Gly Ser Phe Ser Val Gln Trp Ser Asn
             20                  25                  30

Ile Gly Asn Phe Val Val Gly Lys Gly Trp Thr Thr Gly Ser Gly Asn
             35                  40                  45

Ile Val Ile Asn Tyr Ser Gly Ser Tyr Asn Pro Asn Gly Asn Ser Tyr
         50                  55                  60

Leu Cys Val Tyr Gly Trp Thr Arg Asn Pro Leu Val Glu Tyr Tyr Ile
```

```
                 65                  70                  75                  80
Val Glu Asn Trp Gly Thr Tyr Arg Pro Thr Gly Thr Ala Thr Lys Thr
                 85                  90                  95

Val Thr Ser Asp Gly Gly Thr Tyr Asp Ile Tyr Glu Thr Thr Arg Val
                100                 105                 110

Asn Gln Pro Ser Ile Asp Gly Thr Ala Thr Phe Gln Gln Tyr Trp Ser
            115                 120                 125

Val Arg Gln Ser Lys Arg Thr Ser Gly Thr Val Thr Val Thr Asn
            130                 135                 140

His Phe Asp Ala Trp Ala Ser Leu Gly Met Asn Leu Gly Lys Met Tyr
145                 150                 155                 160

Tyr Gln Ile Val Ala Val Glu Gly Tyr Gln Ser Ser Gly Ser Ala Asn
                165                 170                 175

Val Thr Val

<210> SEQ ID NO 20
<211> LENGTH: 184
<212> TYPE: PRT
<213> ORGANISM: Bacillus circulans

<400> SEQUENCE: 20

Ala Ser Thr Asp Tyr Trp Gln Asn Trp Thr Asp Gly Gly Gly Ile Val
1               5                  10                  15

Asn Ala Val Asn Gly Ser Gly Gly Asn Tyr Ser Val Asn Trp Ser Asn
                20                  25                  30

Thr Gly Asn Phe Val Val Gly Lys Gly Trp Thr Thr Gly Ser Pro Phe
            35                  40                  45

Arg Thr Ile Asn Tyr Asn Ala Gly Val Trp Ala Pro Asn Gly Asn Gly
    50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Lys Ser Asp Gly Gly Thr Tyr Asp Ile Tyr Thr Thr Thr Arg
                100                 105                 110

Tyr Asn Ala Pro Ser Ile Asp Gly Asp Arg Thr Thr Phe Thr Gln Tyr
            115                 120                 125

Trp Ser Val Arg Gln Ser Lys Arg Pro Thr Gly Ser Asn Ala Thr Ile
130                 135                 140

Thr Phe Thr Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val
            180

<210> SEQ ID NO 21
<211> LENGTH: 180
<212> TYPE: PRT
<213> ORGANISM: Trichoderma reesei

<400> SEQUENCE: 21

Asn Asn Gly Tyr Phe Tyr Ser Tyr Trp Asn Asp Gly His Gly Gly Val
1               5                  10                  15

Thr Tyr Thr Asn Gly Pro Gly Gly Gln Phe Ser Val Asn Trp Ser Asn
            20                  25                  30
```

```
Ser Gly Asn Phe Val Gly Gly Lys Gly Trp Gln Pro Gly Thr Lys Asn
            35                  40                  45

Lys Val Ile Asn Phe Ser Gly Ser Tyr Asn Pro Asn Gly Asn Ser Tyr
 50                  55                  60

Leu Ser Val Tyr Gly Trp Ser Arg Asn Pro Leu Ile Glu Tyr Tyr Ile
 65                  70                  75                  80

Val Glu Asn Phe Gly Thr Tyr Asn Pro Ser Thr Gly Ala Thr Lys Leu
                 85                  90                  95

Gly Glu Val Thr Ser Asp Gly Ser Val Tyr Asp Ile Tyr Arg Thr Gln
            100                 105                 110

Arg Val Asn Gln Pro Ser Ile Ile Gly Thr Ala Thr Phe Tyr Gln Tyr
            115                 120                 125

Trp Ser Val Arg Arg Asn His Arg Ser Ser Gly Ser Val Asn Thr Ala
130                 135                 140

Asn His Phe Asn Ala Trp Ala Gln Gln Gly Leu Thr Leu Gly Thr Met
145                 150                 155                 160

Asp Tyr Gln Ile Val Ala Val Glu Gly Tyr Phe Ser Ser Gly Ser Ala
                165                 170                 175

Ser Ile Thr Val
            180

<210> SEQ ID NO 22
<211> LENGTH: 176
<212> TYPE: PRT
<213> ORGANISM: Trichoderma reesei

<400> SEQUENCE: 22

Ala Ser Ile Asn Tyr Asp Gln Asn Tyr Gln Thr Gly Gly Gln Val Ser
1                5                  10                  15

Tyr Ser Pro Ser Asn Thr Gly Phe Ser Val Asn Trp Asn Thr Gln Asp
             20                  25                  30

Asp Phe Val Val Gly Val Gly Trp Thr Thr Gly Ser Ser Ala Pro Ile
             35                  40                  45

Asn Phe Gly Gly Ser Phe Ser Val Asn Ser Gly Thr Gly Leu Leu Ser
 50                  55                  60

Val Tyr Gly Trp Ser Thr Asn Pro Leu Val Glu Tyr Tyr Ile Met Glu
 65                  70                  75                  80

Asp Asn His Asn Tyr Pro Ala Gln Gly Thr Val Lys Gly Thr Val Thr
                 85                  90                  95

Ser Asp Gly Ala Thr Tyr Thr Ile Trp Glu Asn Thr Arg Val Asn Glu
            100                 105                 110

Pro Ser Ile Gln Gly Thr Ala Thr Phe Asn Gln Tyr Ile Ser Val Arg
            115                 120                 125

Asn Ser Pro Arg Thr Ser Gly Thr Val Thr Val Gln Asn His Phe Asn
130                 135                 140

Ala Trp Ala Ser Leu Gly Leu His Leu Gly Gln Met Asn Tyr Gln Val
145                 150                 155                 160

Val Ala Val Glu Gly Trp Gly Gly Ser Gly Ser Ala Ser Gln Ser Val
                165                 170                 175

<210> SEQ ID NO 23
<211> LENGTH: 181
<212> TYPE: PRT
<213> ORGANISM: Aspergillus kawachii

<400> SEQUENCE: 23

Ala Gly Ile Asn Tyr Val Gln Asn Tyr Asn Gly Asn Leu Gly Asp Phe
```

-continued

```
1               5               10              15
Thr Tyr Asp Glu Ser Ala Gly Thr Phe Ser Met Tyr Trp Glu Asp Gly
                20                  25                  30

Val Ser Ser Asp Phe Val Val Gly Leu Gly Trp Thr Thr Gly Ser Ser
            35                  40                  45

Asn Ala Ile Thr Tyr Ser Ala Glu Tyr Ser Ala Ser Gly Ser Ser Ser
    50                  55                  60

Tyr Leu Ala Val Tyr Gly Trp Val Asn Tyr Pro Gln Ala Glu Tyr Tyr
65                  70                  75                  80

Ile Val Glu Asp Tyr Gly Asp Tyr Asn Pro Cys Ser Ser Ala Thr Ser
                85                  90                  95

Leu Gly Thr Val Tyr Ser Asp Gly Ser Thr Tyr Gln Val Cys Thr Asp
            100                 105                 110

Thr Arg Thr Asn Glu Pro Ser Ile Thr Gly Thr Ser Thr Phe Thr Gln
                115                 120                 125

Tyr Phe Ser Val Arg Glu Ser Thr Arg Thr Ser Gly Thr Val Thr Val
            130                 135                 140

Ala Asn His Phe Asn Phe Trp Ala Gln His Gly Phe Gly Asn Ser Asp
145                 150                 155                 160

Phe Asn Tyr Gln Val Met Ala Val Glu Ala Trp Ser Gly Ala Gly Ser
                165                 170                 175

Ala Ser Val Thr Ile
            180
```

<210> SEQ ID NO 24
<211> LENGTH: 179
<212> TYPE: PRT
<213> ORGANISM: Streptomyces lividans

<400> SEQUENCE: 24

```
Thr Asp Gly Met Tyr Tyr Ser Phe Trp Thr Asp Gly Gly Gly Ser Val
1               5                   10                  15

Ser Met Thr Leu Asn Gly Gly Gly Ser Tyr Ser Thr Gln Trp Thr Asn
                20                  25                  30

Cys Gly Asn Phe Val Ala Gly Lys Gly Trp Ser Thr Gly Asp Gly Asn
            35                  40                  45

Val Arg Tyr Asn Gly Tyr Phe Asn Pro Val Gly Asn Gly Tyr Gly Cys
    50                  55                  60

Leu Tyr Gly Trp Thr Ser Asn Pro Leu Val Glu Tyr Tyr Ile Val Asp
65                  70                  75                  80

Asn Trp Gly Ser Tyr Arg Pro Thr Gly Thr Tyr Lys Gly Thr Val Ser
                85                  90                  95

Ser Asp Gly Gly Thr Tyr Asp Ile Tyr Gln Thr Thr Arg Tyr Asn Ala
            100                 105                 110

Pro Ser Val Glu Gly Thr Lys Thr Phe Gln Gln Tyr Trp Ser Val Arg
                115                 120                 125

Gln Ser Lys Val Thr Ser Gly Ser Gly Thr Ile Thr Thr Gly Asn His
            130                 135                 140

Phe Asp Ala Trp Ala Arg Ala Gly Met Asn Met Gly Gln Phe Arg Tyr
145                 150                 155                 160

Tyr Met Ile Met Ala Thr Glu Gly Tyr Gln Ser Ser Gly Ser Ser Asn
                165                 170                 175

Ile Thr Val
```

<210> SEQ ID NO 25

```
<211> LENGTH: 187
<212> TYPE: PRT
<213> ORGANISM: Schizophyllum commune

<400> SEQUENCE: 25

Asp Gly Gly Tyr Tyr Tyr Ser Trp Trp Thr Asp Gly Ala Gly Asp Ala
1               5                   10                  15

Thr Tyr Gln Asn Asn Gly Gly Ser Tyr Thr Leu Thr Trp Ser Gly
            20                  25                  30

Asn Asn Gly Asn Leu Val Gly Gly Lys Gly Trp Asn Pro Gly Ala Ala
            35                  40                  45

Ser Arg Ser Ile Ser Tyr Ser Gly Thr Tyr Gln Pro Asn Gly Asn Ser
50                  55                  60

Tyr Leu Ser Val Tyr Gly Trp Thr Arg Ser Ser Leu Ile Glu Tyr Tyr
65                  70                  75                  80

Ile Val Glu Ser Tyr Gly Ser Tyr Asp Pro Ser Ser Ala Ala Ser His
                85                  90                  95

Lys Gly Ser Val Thr Cys Asn Gly Ala Thr Tyr Asp Ile Leu Ser Thr
            100                 105                 110

Trp Arg Tyr Asn Ala Pro Ser Ile Asp Gly Thr Gln Thr Phe Glu Gln
            115                 120                 125

Phe Trp Ser Val Arg Asn Pro Lys Lys Ala Pro Gly Gly Ser Ile Ser
130                 135                 140

Gly Thr Val Asp Val Gln Cys His Phe Asp Ala Trp Lys Gly Leu Gly
145                 150                 155                 160

Met Asn Leu Gly Ser Glu His Asn Tyr Gln Ile Val Ala Thr Glu Gly
                165                 170                 175

Tyr Gln Ser Ser Gly Thr Ala Thr Ile Thr Val
            180                 185

<210> SEQ ID NO 26
<211> LENGTH: 179
<212> TYPE: PRT
<213> ORGANISM: Cochliobolus carbone

<400> SEQUENCE: 26

His Asn Gly Cys Phe Trp Ser Trp Trp Ser Asp Gly Ala Arg Ala
1               5                   10                  15

Thr Tyr Thr Asn Gly Ala Gly Gly Ser Tyr Ser Val Ser Trp Gly Ser
            20                  25                  30

Gly Gly Asn Leu Val Gly Gly Lys Gly Trp Asn Pro Gly Thr Ala Arg
            35                  40                  45

Thr Ile Thr Tyr Ser Gly Thr Tyr Asn Tyr Asn Gly Asn Ser Tyr Leu
50                  55                  60

Ala Val Tyr Gly Trp Thr Arg Asn Pro Leu Val Glu Tyr Tyr Val Val
65                  70                  75                  80

Glu Asn Phe Gly Thr Tyr Asp Pro Ser Ser Gln Ser Gln Asn Lys Gly
                85                  90                  95

Thr Val Thr Ser Asp Gly Ser Ser Tyr Lys Ile Ala Gln Ser Thr Arg
            100                 105                 110

Thr Asn Gln Pro Ser Ile Asp Gly Thr Arg Thr Phe Gln Gln Tyr Trp
            115                 120                 125

Ser Val Arg Gln Asn Lys Arg Ser Ser Gly Ser Val Asn Met Lys Thr
130                 135                 140

His Phe Asp Ala Trp Ala Ser Lys Gly Met Asn Leu Gly Gln His Tyr
145                 150                 155                 160
```

```
Tyr Gln Ile Val Ala Thr Glu Gly Tyr Phe Ser Gly Asn Ala Gln
                165                 170                 175

Ile Thr Val

<210> SEQ ID NO 27
<211> LENGTH: 198
<212> TYPE: PRT
<213> ORGANISM: Ruminococcus flavefaciens

<400> SEQUENCE: 27

Val Gly Gly Tyr Asp Tyr Glu Met Trp Asn Gln Asn Gly Gln Gly Gln
1               5                   10                  15

Ala Ser Met Asn Pro Gly Ala Gly Ser Phe Thr Cys Ser Trp Ser Asn
            20                  25                  30

Ile Glu Asn Phe Leu Ala Arg Met Gly Lys Asn Tyr Asp Ser Gln Lys
        35                  40                  45

Lys Asn Tyr Lys Ala Phe Gly Asn Ile Val Leu Thr Tyr Asp Val Glu
50                  55                  60

Tyr Thr Pro Arg Gly Asn Ser Tyr Met Cys Val Tyr Gly Trp Thr Arg
65                  70                  75                  80

Asn Pro Leu Met Glu Tyr Tyr Ile Val Glu Gly Trp Gly Asp Trp Arg
                85                  90                  95

Pro Pro Gly Asn Asp Gly Glu Val Lys Gly Thr Val Ser Ala Asn Gly
            100                 105                 110

Asn Thr Tyr Asp Ile Arg Lys Thr Met Arg Tyr Asn Gln Pro Ser Leu
        115                 120                 125

Asp Gly Thr Ala Thr Phe Pro Gln Tyr Trp Ser Val Arg Gln Thr Ser
130                 135                 140

Gly Ser Ala Asn Asn Gln Thr Asn Tyr Met Lys Gly Thr Ile Asp Val
145                 150                 155                 160

Thr Lys His Phe Asp Ala Trp Ser Ala Ala Gly Leu Asp Met Ser Gly
                165                 170                 175

Thr Leu Tyr Glu Val Ser Leu Asn Ile Glu Gly Tyr Arg Ser Asn Gly
            180                 185                 190

Ser Ala Asn Val Lys Ser
            195

<210> SEQ ID NO 28
<211> LENGTH: 186
<212> TYPE: PRT
<213> ORGANISM: Clostridium stercorarium

<400> SEQUENCE: 28

His Gly Gly Tyr Asp Tyr Glu Leu Trp Lys Asp Tyr Gly Asn Thr Ile
1               5                   10                  15

Met Glu Leu Asn Asp Gly Gly Thr Phe Ser Cys Gln Trp Ser Asn Ile
            20                  25                  30

Gly Asn Ala Leu Phe Arg Lys Gly Arg Lys Phe Asn Ser Asp Lys Thr
        35                  40                  45

Tyr Gln Glu Leu Gly Asp Ile Val Val Glu Tyr Gly Cys Asp Tyr Asn
50                  55                  60

Pro Asn Gly Asn Ser Tyr Leu Cys Val Tyr Gly Trp Thr Arg Asn Pro
65                  70                  75                  80

Leu Val Glu Tyr Tyr Ile Val Glu Ser Trp Gly Ser Trp Arg Pro Pro
                85                  90                  95

Gly Ala Thr Pro Lys Gly Thr Ile Thr Gln Trp Met Ala Gly Thr Tyr
            100                 105                 110
```

```
Glu Ile Tyr Glu Thr Thr Arg Val Asn Gln Pro Ser Ile Asp Gly Thr
        115                 120                 125

Ala Thr Phe Gln Gln Tyr Trp Ser Val Arg Thr Ser Lys Arg Thr Ser
    130                 135                 140

Gly Thr Ile Ser Val Thr Glu His Phe Lys Gln Trp Glu Arg Met Gly
145                 150                 155                 160

Met Arg Met Gly Lys Met Tyr Glu Val Ala Leu Thr Val Glu Gly Tyr
                165                 170                 175

Gln Ser Ser Gly Tyr Ala Asn Val Tyr Lys
            180                 185

<210> SEQ ID NO 29
<211> LENGTH: 185
<212> TYPE: PRT
<213> ORGANISM: Clostridium saccharobytylicum

<400> SEQUENCE: 29

Asn Gly Gly Tyr Asp Tyr Glu Leu Trp Lys Asp Tyr Gly Asn Thr Ser
1               5                   10                  15

Met Thr Leu Lys Asn Gly Gly Ala Phe Ser Cys Gln Trp Ser Asn Ile
            20                  25                  30

Gly Asn Ala Leu Phe Arg Lys Gly Lys Lys Phe Asn Asp Thr Gln Thr
                35                  40                  45

Tyr Lys Gln Leu Gly Asn Ile Ser Val Asn Tyr Asp Cys Asn Tyr Gln
    50                  55                  60

Pro Tyr Gly Asn Ser Tyr Leu Cys Val Tyr Gly Trp Thr Ser Ser Pro
65                  70                  75                  80

Leu Val Glu Tyr Tyr Ile Val Asp Ser Trp Gly Ser Trp Arg Pro Pro
                85                  90                  95

Gly Gly Thr Ser Lys Gly Thr Ile Thr Val Asp Gly Gly Ile Tyr Asp
            100                 105                 110

Ile Tyr Glu Thr Thr Arg Ile Asn Gln Pro Ser Ile Gln Gly Asn Thr
        115                 120                 125

Thr Phe Lys Gln Tyr Trp Ser Val Arg Arg Thr Lys Arg Thr Ser Gly
    130                 135                 140

Thr Ile Ser Val Ser Lys His Phe Ala Ala Trp Glu Ser Lys Gly Met
145                 150                 155                 160

Pro Leu Gly Lys Met His Glu Thr Ala Phe Asn Ile Glu Gly Tyr Gln
                165                 170                 175

Ser Ser Gly Lys Ala Asp Val Asn Ser
            180                 185
```